United States Patent [19]

Cragoe, Jr. et al.

[11] 4,225,609

[45] Sep. 30, 1980

[54] INTERPHENYLENE 9-THIA-11-OXO-12-AZA-PROSTANOIC ACIDS

[75] Inventors: Edward J. Cragoe, Jr.; Ta-jyh Lee; John B. Bicking, all of Lansdale, Pa.

[73] Assignee: Merck & Co., Inc., Rahway, N.J.

[21] Appl. No.: 938,129

[22] Filed: Aug. 30, 1978

Related U.S. Application Data

[63] Continuation-in-part of Ser. No. 846,065, Oct. 27, 1977, abandoned.

[51] Int. Cl.$^2$ ............................................. C07D 277/04
[52] U.S. Cl. .................................... 424/270; 548/186; 548/187
[58] Field of Search ................. 424/270; 260/306.7 C, 260/306.7 R; 548/186, 187

[56] References Cited

U.S. PATENT DOCUMENTS

| 3,881,017 | 4/1975 | Vlattas | 260/295 R |
| 3,883,659 | 5/1975 | Vlattas | 260/295 R |
| 4,022,794 | 5/1977 | Smith et al. | 260/295 C |

FOREIGN PATENT DOCUMENTS

828994 1/1975 Belgium.
2521517 5/1974 Fed. Rep. of Germany.
2422498 12/1974 Fed. Rep. of Germany.

OTHER PUBLICATIONS

Morton et al, Abstract of Paper, 172nd ACS National Meeting, Aug. 30–Sep. 3, 1976, Chemical Society Division of Medicinal Chemistry.
Ambros et al, Prostaglandins, vol. 10, pp. 661–666, (1975).

*Primary Examiner*—Nicholas S. Rizzo
*Attorney, Agent, or Firm*—Thomas E. Arther; Mario A. Monaco; Rudolph J. Anderson, Jr.

[57] ABSTRACT

This invention relates to novel interphenylene 9-thia-11-oxo-12-azaprostanoic acid compounds, salts, and derivatives thereof. These compounds are exceptionally potent renal vasodilators and antihypertensives which are active when administered orally but which have a more specific type of biological activity than that of many of the natural prostaglandins and their synthetic analogs or derivatives.

65 Claims, No Drawings

INTERPHENYLENE 9-THIA-11-OXO-12-AZA-PROSTANOIC ACIDS

RELATIONSHIP TO OTHER APPLICATIONS

This application is a continuation-in-part of U.S. Ser. No. 846,065 filed Oct. 27, 1977, now abandoned.

DESCRIPTION OF THE INVENTION

This invention relates to novel interphenylene 9-thia-11-oxo-12-azaprostanoic acids, salts, and derivatives which are represented by the following formula:

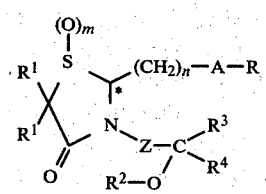   I wherein R is selected from the group consisting of carboxy and a carboxy salt which incorporates a pharmaceutically acceptable cation, such as metal cations derived from alkali metals, alkaline earth metals, and amines such as ammonia, primary and secondary amines and quaternary ammonium hydroxides. Especially preferred metal cations are those derived from alkali metals, e.g., sodium, potassium, lithium, and the like, and alkaline earth metals, e.g., calcium, magnesium, and the like, and other metals, i.e., aluminum, iron, and zinc.

Pharmaceutically acceptable cations derived from primary, secondary, or tertiary amines, or quaternary ammonium hydroxides are methylamine, dimethylamine, 1-methylpiperazine, trimethylamine, ethylamine, N-methylhexylamine, benzylamine, α-phenethylamine, ethylenediamine, piperidine, morpholine, pyrrolidine, 1,4-dimethylpiperazine, ethanolamine, diethanolamine, triethanolamine, tris(hydroxymethyl)aminomethane, N-methylglucamine, N-methylglucosamine, ephedrine, procaine, tetramethylammonium hydroxide, tetraethylammonium hydroxide, benzyltrimethylammonium hydroxide, and the like.

R is also selected from alkoxycarbonyl, e.g., a carboxy ester of the formula —COOR$^5$ wherein R$^5$ is alkyl having 1-10 carbon atoms.

R is further selected from the group

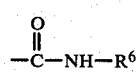

wherein R$^6$ is amino (NH$_2$) or methylsulfonyl (CH$_3$SO$_2$).

A is a divalent monocyclic aromatic or a 5-membered sulfur or oxygen containing heterocyclic ring preferably a p-phenylene or a m-phenylene or substituted phenylene derivatives in which one or two of the phenylene hydrogens is replaced by a methyl or a halo, preferably chloro, substitutent or 2,5-thienylene or 2,5-furylene. Examples of such substituents are p-phenylene

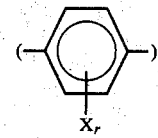

or m-phenylene

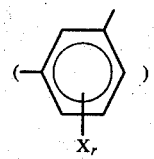

where X is either hydrogen or chloro or methyl, and r is 0, 1, or 2, or 2,5-thienylene

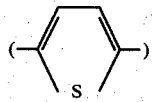

or 2,5-furylene

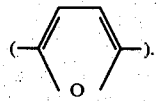

n is 3 or 4.
m is 0, 1, or 2.
R$^1$ is hydrogen, an isotope thereof especially deuterium, or methyl.
Z is alkylene or unsaturated alkylene of from 2–3 carbon atoms preferably ethylene (—CH$_2$CH$_2$—), trimethylene (—CH$_2$CH$_2$CH$_2$—), cis-propenylene

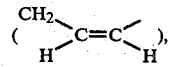

trans-propenylene

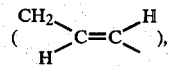

or propynylene (—CH$_2$C≡C—).
R$^2$ is hydrogen or lower alkanoyl especially acetyl.
R$^3$ is hydrogen or a straight chain lower alkyl of one to three carbon atoms.
R$^4$ is lower straight chain or branched alkyl having from 3 to 7 carbon atoms (especially propyl, butyl, amyl, isoamyl, heptyl, and 1,1-dimethylpentyl), unsaturated lower alkyl including 4-pentenyl, substituted lower alkyl such as polyfluoroalkyl, as for example 5,5,5-trifluoropentyl, and lower alkoxy methylene such as —CH$_2$—O—R$^7$ preferably where R$^7$ is selected from the group consisting of lower alkyl, straight or branched, with from 2 to 5 carbon atoms; or R$^3$ and R$^4$ taken together with the carbon atom connecting R$^3$ and R$^4$ is a cyclic substituent comprising an alicyclic ring, bridged or unbridged, of from 5 to 9 carbon atoms such as cyclopentyl, cyclohexyl, cyclooctyl, or bicyclo[3.3.1]nonyl, or a heterocyclic ring containing sulfur or oxygen and with from 5 to 7 ring-forming carbon atoms such as tetrahydropyranyl or tetrahydrothiopyranyl.

A preferred sub-group of the compounds of this invention are compounds of the formula:

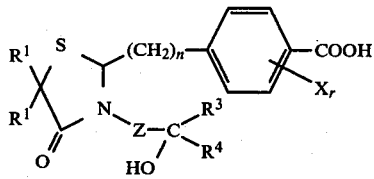

wherein X is chlorine or methyl; r is 0, 1, or 2; n is 3 or 4; $R^1$ is hydrogen, deuterium, or methyl; Z is ethylene, trimethylene, cis or trans-propenylene, or propynylene; $R^3$ is hydrogen or lower alkyl of 1-3 carbon atoms; and $R^4$ is 4-pentenyl, 5,5,5-trifluoropentyl, or lower straight or branched chain alkyl of 3-7 carbon atoms. Examples of compounds included within this group are:
4-{3-[3-(3-hydroxyoctyl)-4-oxo-2-thiazolidinyl]propyl}benzoic acid;
4-{3-[3-(3-hydroxydecyl)-4-oxo-2-thiazolidinyl]propyl}benzoic acid;
4-{3-[3-(3-hydroxy-4,4-dimethyloctyl)-4-oxo-2-thiazolidinyl]propyl}benzoic acid;
4-{3-[3-(3-hydroxy-7-octenyl)-4-oxo-2-thiazolidinyl]propyl}benzoic acid;
4-{3-[3-(3-hydroxy-8,8,8-trifluorooctyl)-4-oxo-2-thiazolidinyl]propyl}benzoic acid; and
4-{3-[3-(3-hydroxy-3-methyloctyl)-4-oxo-2-thiazolidinyl]propyl}benzoic acid.

Another preferred sub-group of the compounds of this invention are selected from the group consisting of a compound of the formula:

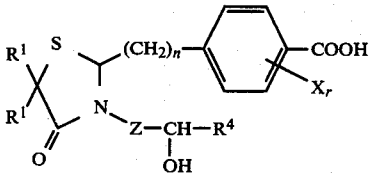

wherein X is chlorine or methyl; r is 0, 1, or 2; n is 3 or 4; $R^1$ is hydrogen, deuterium, or methyl; Z is ethylene, trimethylene, cis or trans-propenylene, or propynylene; and $R^4$ is $CH_2OR^7$ wherein $R^7$ is lower straight or branched chain alkyl of 2-5 carbon atoms. An example of such a compound is 4-{3-[3-(3-hydroxy-4-propoxybutyl)-4-oxo-2-thiazolidinyl]propyl}benzoic acid.

Another preferred sub-group of the compounds of this invention is selected from the group consisting of a compound of the formula:

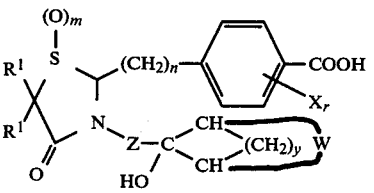

wherein X is chlorine or methyl; r is 0, 1, or 2; n is 3 or 4; m is 0, 1, or 2; $R^1$ is hydrogen, deuterium, or methyl; Z is ethylene, trimethylene, propenylene, or propynylene; y is 0, 2, or 3; and W is polymethylene of 2-6 carbon atoms. Examples of such compounds are:
4-{3-[3-[2-(1-hydroxycyclohexyl)ethyl]-4-oxo-2-thiazolidinyl]propyl}benzoic acid
4-{3-[3-[2-(1-hydroxycyclopentyl)ethyl]-4-oxo-2-thiazolidinyl]propyl}benzoic acid
4-{3-[3-[2-(1-hydroxycycloheptyl)ethyl]-4-oxo-2-thiazolidinyl]propyl}benzoic acid
4-{3-[3-[2-(1-hydroxy-4,4-dimethylcyclohexyl)ethyl]-4-oxo-2-thiazolidinyl]propyl}benzoic acid
4-{3-[3-[2-(9-hydroxy-9-bicyclo[3.3.1]nonyl)ethyl]-4-oxo-2-thiazolidinyl]propyl}benzoic acid
4-{4-[3-[2-(1-hydroxycyclohexyl)ethyl]-4-oxo-2-thiazolidinyl]butyl}benzoic acid
4-{3-[3-[3-(1-hydroxycyclohexyl)propyl]-4-oxo-2-thiazolidinyl]propyl}benzoic acid
4-{3-[3-[3-(1-hydroxycyclohexyl)-(Z)-2-propenyl]-4-oxo-2-thiazolidinyl]propyl}benzoic acid
4-{3-[3-[3-(1-hydroxycyclohexyl)-(E)-2-propenyl]-4-oxo-2-thiazolidinyl]propyl}benzoic acid
4-{3-[3-[3-(1-hydroxycyclohexyl)-2-propynyl]-4-oxo-2-thiazolidinyl]propyl}benzoic acid
4-{3-[3-[2-(1-hydroxycyclohexyl)ethyl]-4-oxo-2-thiazolidinyl]propyl}-3-chlorobenzoic acid
4-{3-[3-[2-(1-hydroxycyclohexyl)ethyl]-4-oxo-2-thiazolidinyl]propyl}-2-chlorobenzoic acid
4-{3-[3-[2-(1-hydroxycyclohexyl)ethyl]-4-oxo-2-thiazolidinyl]propyl}-3-methylbenzoic acid
4-{3-[3-[2-(1-hydroxycyclohexyl)ethyl]-1,4-dioxo-2-thiazolidinyl]propyl}benzoic acid
4-{3-[3-[2-(1-hydroxycyclohexyl)ethyl]-1,1,4-trioxo-2-thiazolidinyl]propyl}benzoic acid
4-{3-[3-[2-(1-hydroxycyclohexyl)ethyl]-5,5-dimethyl-4-oxo-2-thiazolidinyl]propyl}benzoic acid
4-{3-[3-[2-(1-hydroxycyclohexyl)ethyl]-5,5-dideuterio-4-oxo-2-thiazolidinyl]propyl}benzoic acid A still further preferred sub-group of this invention is selected from the group consisting of a compound of the formula:

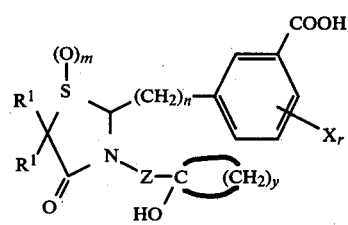

wherein X is chlorine or methyl; r is 0, 1, or 2; n is 3 or 4; m is 0, 1, or 2; $R^1$ is hydrogen or methyl; Z is ethylene, trimethylene, propenylene, or propynylene; and y is 4 to 8. An example of a compound of this sub-group is 3-{3-[3-[2-(1-hydroxycyclohexyl)ethyl]-4-oxo-2-thiazolidinyl]propyl}benzoic acid.

Still further sub-groups of preferred compounds of this invention are represented by the formulas:

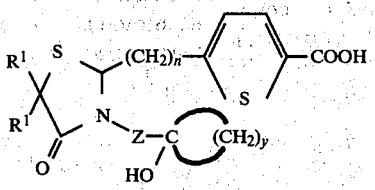

wherein n is 3 or 4; $R^1$ is hydrogen or methyl; Z is ethylene, trimethylene, propenylene, or propynylene; and y is 4 to 8;

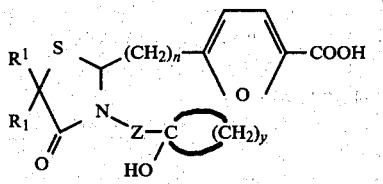

wherein n is 3 or 4; $R^1$ is hydrogen or methyl; Z is ethylene, trimethylene, propenylene, or propynylene; and y is 4 to 8; and

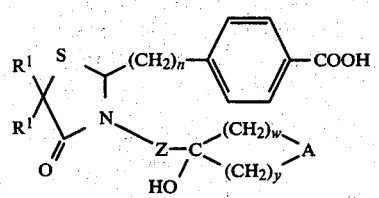

wherein n is 3 or 4; $R^1$ is hydrogen or methyl; Z is ethylene, trimethylene, propenylene, or propynylene; w and y are each 1 to 5 with the sum of w and y being from 4 to 6; and A is oxygen or sulfur.

The carbon atom in the thiazolidinone ring marked by an asterisk (*) is asymmetric in all compounds of this invention. In compounds wherein $R^3$ and $R^4$ are dissimilar, the carbon atom bearing these groups is asymmetric. Thus, the compounds of this invention are obtained as racemates when only the former carbon is asymmetric and they are obtained as mixtures of diastereomers when both carbon atoms are asymmetric. This invention includes the separate stereoisomers which are components of these mixtures of isomers. The separate stereoisomers have biological activity similar to those of the racemates and diastereomeric mixtures, which biological activity varies from compound to compound.

BACKGROUND OF THE INVENTION

The compounds of formula I are described as interphenylene 9-thia-11-oxo-12-azaprostanoic acids and derivatives as a means of describing the structural relationship to prostanoic acid, which has the carbon skeleton of the natural prostaglandins as shown in the following formula:

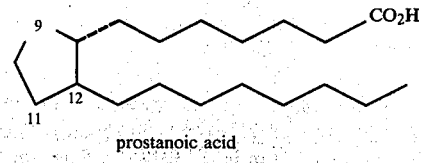

prostanoic acid

The prostaglandins constitute a class of highly functionalized $C_{20}$ fatty acids. They have been shown to occur extensively in low concentrations in mammalian tissues where they are both rapidly anabolized and catabolized and to exhibit a broad spectrum of pharmacological activities including prominent roles in (a) functional hyperemia, (b) the inflammatory response, (c) the central nervous system, (d) transport of water and electrolytes, and (e) regulation of cyclic AMP. Further details concerning the prostaglandins can be found in recent reviews of their chemistry [J. E. Pike, FORTSCHR. CHEM ORG. NATURST., 28, 313 (1970) and G. F. Bundy, A. REP. IN MED. CHEM., 7, 157 (1972)]; biochemistry [J. W. Hinman, A. REV. BIOCHEM., 41, 161 (1972)]; pharmacology [J. R. Weeks, A. REV. PHARM., 12, 317 (1972)]; physiological significance [E. W. Horton, PHYSIOL. REV. 49, 122 (1969)]; and general clinical application [J. E. Hinman, POSTGRAD MED. J. 46, 562 (1970)].

The potential application of natural prostaglandins as medicinally useful therapeutic agents in various mammalian disease states is obvious but suffers from three formidable major disadvantages, namely, (a) prostaglandins are known to be rapidly metabolized in vivo in various mammalian tissues to a variety of metabolites which are devoid of the desired original biological activities, (b) the natural prostaglandins are inherently devoid of biological specificity which is requisite for a successful drug (since this property is responsible for intolerable side effects), and (c) although limited quantities of prostaglandins are presently produced by both chemical and biochemical processes, their production cost is extremely high; and consequently, the availability is quite restricted.

Our interest has, therefore, been to synthesize novel compounds with the following unique advantages: (a) simplicity of synthesis leading to low cost of production; (b) specificity of biological activity; and (c) metabolic stability so that activity can be obtained on oral as well as parenteral administration.

In accordance with the present invention, there is provided a novel group of aza-prostanoic acids of formula I hereinabove. Surprisingly, the compounds of the present invention have a specific range of biological activities and *do not* possess the broad spectrum of biological activity possessed by the natural prostaglandins and their analogs. The compounds of the present invention, for example, are completely inactive in the mouse ovary prostaglandin assay which measures increases in cellular cyclic adenosine monophosphate levels ordinarily caused by prostaglandins and related compounds.

The compounds of the present invention, in addition, are highly potent, orally effective renal vasodilators having a sustained biological action but with reduced side effects and, therefore, are useful for the treatment of patients with renal impairment. Included in this group are patients with hypertension, renal failure, congestive heart failure, glomerulonephritis, uremia, and chronic renal insufficiency. The compounds of this invention by virtue of their renal vasodilatory activity improve renal function both when used alone or in conjunction with other renal agents. An example of a compound with high renal vasodilatory activity is 4-{3-[3-[2-(1-hydroxycyclohexyl)ethyl]-4-oxo-2-thiazolidinyl]propyl}benzoic acid.

The compounds of the present invention are also orally effective antihypertensive agents and as such are useful in reducing blood pressure in individuals affected by this problem. The compounds of the present invention are surprisingly potent in their antihypertensive effect when compared with structurally related compounds.

The compounds of this invention have adjunctive properties which give them added utility for the treatment of renal disease. Such properties include antiasthmatic (bronchorelaxant), cardiotonic, and immunoregulant activities.

A further area of usefulness of the compounds of this invention is in the prevention of organ transplant rejection.

The compounds of this invention can be administered intravenously, subcutaneously, intramuscularly, orally, rectally, or by aerosolization in the form of sterile implants for long action. They can be formulated in any of a number of pharmaceutical compositions and nontoxic carriers to this end.

The pharmaceutical compositions can be sterile, injectable suspensions or solutions, or solid, orally administrable, pharmaceutically acceptable tablets or capsules; the compositions can also be intended for sublingual administration, or for suppository use. It is especially advantageous to formulate compositions in dosage unit forms for ease and economy of administration and uniformity of dosage. "Dosage unit form" as a term used herein refers to physically discrete units suitable as unitary dosages for animal and human subjects, each unit containing a predetermined quantity of active material calculated to produce the desired biological effect in association with the required pharmaceutical means.

Illustratively, a sterile injectable composition can be in the form of aqueous or oleagenous suspensions or solutions.

The sterile, injectable composition can be aqueous or oleagenous suspension or solution. Suspensions can be formulated according to the known art using suitable dispersing and wetting agents and suspending agents. Solutions are similarly prepared from the salt form of the compound. For the laboratory animals, we prefer to use incomplete Freund's adjuvant or sterile saline (9%) as carrier. For human parenteral use, such as intramuscularly, intravenously, or by regional perfusion, the diluent can be a sterile aqueous vehicle containing a preservative, for example, methylparaben, propylparaben, phenol, and chlorobutanol. The aqueous vehicle can also contain sodium chloride, preferably in an amount to be isotonic, as well as a suspending agent, for example, gum arabic, polyvinyl pyrrolidone, methyl cellulose, acetylated monoglyceride (available commercially as Myvacet from Distillation Products Industry, a division of Eastman Kodak Company), monomethyl glyceride, dimethyl glyceride, or a moderately high molecular weight polysorbitan (commercially available under the tradenames Tween or Span from Atlas Powder Company, Wilmington, Delaware). Other materials employed in the preparation of chemotherapeutic compositions containing the compound may include glutathione, 1,2-propanediol, glycerol, and glucose. In addition, the pH of the composition is adjusted by use of an aqueous solution such as tris(hydroxymethyl)aminomethane (tris buffer).

Oily pharmaceutical carriers can also be used, since they dissolve the compound and permit high doses. Many oily carriers are commonly employed in pharmaceutical use, such as, for example, mineral oil, lard, cottonseed oil, peanut oil, sesame oil, or the like.

It is preferred to prepare the compositions, whether aqueous or oils, in a concentration in the range of from 2-50 mg./ml. Lower concentrations require needless quantities of liquid. Higher concentrations than 50 mg./ml. are difficult to maintain and are preferably avoided.

Oral administration forms of the drug can also be prepared for laboratory animals or human patients provided that they are encapsulated for delivery in the gut. The drug is subject to enzymatic breakdown in the acid environment of the stomach. The same dosage levels can be used as for injectable forms; however, even higher levels can be used to compensate for biodegradation in the transport. Generally, a solid unit dosage form can be prepared containing from 0.05 mg. to 10 mg. active ingredient and preferably from 0.1 mg. to 1 mg. of active ingredient.

Whatever the mode of administration, doses in the range of about 0.05 to 10 milligrams per kilogram of body weight, preferably 0.1 to 1 mg., administered one to four times per day are used, the exact dose depending on the age, weight, and condition of the patient, and the frequency and route of administration.

The low cost and ready accessibility of the compounds of this invention make them particularly promising for applications in veterinary medicine in which field their utilities are comparable to those in human medicine.

Processes for the Synthesis of the Compounds of this Invention

One of the preferred groups of compounds of the present invention are the carboxylic acids represented by formula II:

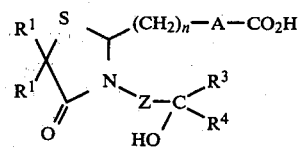

wherein A, n, $R^1$, Z, $R^3$, and $R^4$ are as previously defined. These acids can be synthesized by any of three processes which will now be described.

PROCESS 1

Step 1

An aldehyde of formula III:

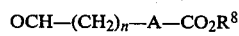

$$OCH-(CH_2)_n-A-CO_2R^8 \qquad III$$

wherein A and n are as previously defined and $R^8$ is straight chain lower alkyl (preferably methyl or ethyl), is condensed with a primary amine of formula IV:

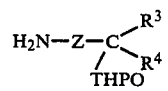

wherein Z, $R^3$, and $R^4$ are as previously defined and THP is the tetrahydro-2H-pyran-2-yl group. The product of this condensation is the imine of formula V:

$$\underset{\text{THPO}}{\overset{\text{HC}}{\underset{\parallel}{\text{N}}}}\overset{(CH_2)_n-A-CO_2R^8}{\underset{Z-C<^{R^3}_{R^4}}{}}\quad V$$

wherein all groups are as defined previously.

According to the preferred practice, aldehyde III is added to amine IV while maintaining a temperature preferably at 0°–5° C. Anhydrous sodium sulfate is then added, and the mixture stirred at room temperature for a period of 0.5 to 4 hours. The solid is removed by filtration. The filtrate consists of the crude imine V which is used in the next step.

Step 2

A mercaptoacetic acid of formula VI:

$$\underset{R^{1'}}{\overset{R^1}{>}}\underset{\underset{CO_2H}{|}}{C}\overset{SH}{<}\quad VI$$

wherein $R^1$ is as defined previously, is condensed with imine V to yield the thiazolidinone of formula VII:

$$\underset{R^{1'}}{\overset{R^1}{>}}\underset{O}{\overset{S}{<}}\underset{N}{>}\overset{(CH_2)_n-A-CO_2R^8}{\underset{Z-C<^{R^3}_{R^4}}{\underset{THPO}{}}}\quad VII$$

This condensation is most advantageously conducted by dissolving mercaptoacetic acid VI and imine V in a solvent such as benzene or toluene and boiling the solution under reflux in a Dean-Stark or similar apparatus for removal of the water formed in the condensation.

Alternately, mercaptoacetic acid VI may be replaced by its methyl or ethyl ester. In this case, the ester of mercaptoacetic acid VI and imine V are dissolved in benzene or toluene and the solution boiled under reflux for a period of 3 to 12 hours.

Step 3

Thiazolidinone VII is treated with a trace of strong acid such as concentrated hydrochloric acid in a protic solvent, preferably methanol or ethanol, at room temperature for a period of 1 to 24 hours. This treatment hydrolyzes the protecting tetrahydropyranyl (THP) group and produces the thiazolidinone of formula VIII:

$$\underset{R^{1'}}{\overset{R^1}{>}}\underset{O}{\overset{S}{<}}\underset{N}{>}\overset{(CH_2)_n-A-CO_2R^8}{\underset{Z-C<^{R^3}_{R^4}}{\underset{HO}{}}}\quad VIII$$

wherein all groups are as defined previously.

Step 4

Thiazolidinone ester VIII is subjected to basic hydrolysis (dilute aqueous NaOH, LiOH, or KOH in methanol, ethanol, or tetrahydrofuran) at room temperature to remove the protecting ester function and produce the thiazolidinone carboxylic acid of formula II, one of the products of this invention.

PROCESS 2

This process is particularly useful for the preparation of those products of formula II wherein Z is trimethylene, cis and trans-propenylene, and propynylene, i.e., wherein a three-carbon chain joins the nitrogen atom of the thiazolidinone ring and the carbon bearing OH.

Step 1

An aldehyde of formula III above is condensed with a mercaptoacetamide of formula XI:

$$\underset{R^{1'}}{\overset{R^1}{>}}\underset{\underset{CONH_2}{|}}{C}\overset{SH}{<}\quad XI$$

wherein $R^1$ is as defined previously to yield a thiazolidinone ester of formula XII:

$$\underset{R^{1'}}{\overset{R^1}{>}}\underset{O}{\overset{S}{<}}\underset{NH}{>}\overset{(CH_2)_n-A-CO_2R^8}{}\quad XII$$

wherein all groups are as defined previously.

The condensation is advantageously conducted by dissolving amide XI and aldehyde III along with a trace of a strong acid catalyst such as p-toluenesulfonic acid in a suitable solvent such as benzene or toluene and boiling the solution under reflux in a Dean-Stark apparatus for removal of the water formed in the condensation.

Step 2

Thiazolidinone ester XII is converted to its anion by treatment with a strong base, preferably sodium hydride, in an aprotic solvent such as dimethylformamide (DMF) or solvent combination such as DMF-benzene or DMF-toluene. The anion is alkylated by reaction at 35°–75° C. for a period of 3 to 10 hours with a halide of formula XIII:

$$X-Z-\underset{PO}{\overset{R^3}{C<^{R^3}_{R^4}}}\quad XIII$$

wherein X is chlorine, bromine, or iodine, P is an acetyl or tetrahydropyranyl protecting group, and $R^3$ and $R^4$ are as defined previously. The product of this alkylation is the thiazolidinone ester of formula XIV:

$$\underset{R^{1'}}{\overset{R^1}{>}}\underset{O}{\overset{S}{<}}\underset{N}{>}\overset{(CH_2)_n-A-CO_2R^8}{\underset{Z-C<^{R^3}_{R^4}}{\underset{PO}{}}}\quad XIV$$

Step 3

This step is necessary only when protecting group P in thiazolidinone XIV is tetrahydropyranyl. In this case, XIV (P=tetrahydropyranyl) is treated with a trace of an acid catalyst (concentrated hydrochloric acid, p-toluenesulfonic acid, pyridinium tosylate) in a protic solvent, preferably methanol or ethanol, at room temperature for a period of 1 to 24 hours. This treatment produces the thiazolidinone ester of formula VIII above.

Step 4

The thiazolidinone esters XIV (P=acetyl) or VIII are subjected to basic hydrolysis as described in Step 4 of Process 1. The thiazolidinone carboxylic acid of formula II is thereby produced.

PROCESS 3

This process is useful for the preparation of only those compounds of formula II in which the alcohol function (C—OH) is tertiary. Thus, $R^3$ is limited to lower alkyl and may be joined with $R^4$ to form alicyclic or heterocyclic rings as described in the specification. This process is further limited to the preparation of those compounds of formula II in which Z is saturated, i.e., is ethylene or trimethylene.

Step 1

Thiazolidinone ester XII above is converted to its anion as described in Step 2 of Process 2. The anion in solution is alkylated by reaction a 35°–75° C. for a period of 3 to 10 hours with an olefinic halide of formula XV:

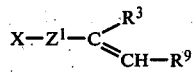

wherein X is bromine or iodine, $Z^1$ is ethylene or trimethylene, $R^3$ is lower alkyl, and $R^9$ is alkyl with from 2 to 6 carbon atoms, 3-butenyl, or 4,4,4-trifluorobutyl. Further, when $R^9$ is alkyl, $R^3$ and $R^9$ can be joined either directly or through an oxygen or sulfur atom to form, along with C=CH, an alicyclic ring of from 5 to 9 carbon atoms or a heterocyclic ring containing oxygen or sulfur and with from 5 to 7 ring-forming carbon atoms. The product of this alkylation of compound XII is the olefinic thiazolidinone ester of formula XVI:

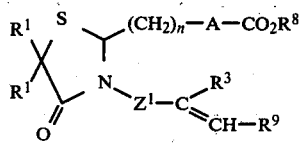

Step 2

Olefinic thiazolidinone ester XVI is treated with an excess of trifluoroacetic acid at temperatures from 10° to 25° C. and for a period of two to six hours. Trifluoroacetic acid adds to the olefinic bond in the Markownikoff manner to yield the thiazolidinone ester of formula XVII:

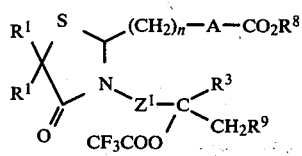

wherein all groups are as defined previously.

Step 3

Thiazolidinone ester XVII is subjected to basic hydrolysis as described in Step 4 of Process 1. A thiazolidinone carboxylic acid of formula IIa:

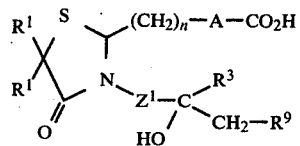

wherein all groups are as defined previously are produced. The acids IIa are seen to be a sub-class of the products of this invention of formula II.

Alternatively, the order of reactions in Steps 2 and 3 can be reversed. Thus, under analogous reaction conditions, olefinic thiazolidinone ester XVI can be hydrolyzed to the acid of formula XVIII:

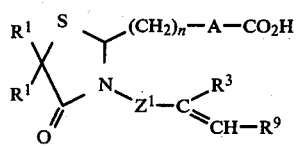

Acid XVIII can be treated with trifluoroacetic acid as described above to give the trifluoroacetoxy acid of formula XIX:

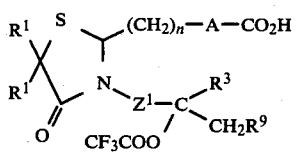

Compound XIX can then be subjected to hydrolysis, preferably basis hydrolysis, to remove the trifluoroacetyl group and yield the products of this invention of formula IIa.

DERIVATIZATION OF PRODUCTS OF FORMULA II FROM THE PRINCIPAL PROCESSES

The processes described hereinabove lead to the production of carboxylic acids of formula II. Often these are produced by a process which requires hydrolysis of a carboxy ester at the final stage or at some intermediate stage of the process. The hydrolysis of the esters of the acids of formula II or of the intermediate carboxy esters may be carried out under acid or basic conditions. Basic hydrolysis is preferred using dilute aqueous solutions of NaOH, LiOH, or KOH in methanol, ethanol, or tetrahydrofuran at room temperature, but, if desired, acid hydrolysis using a solution of a small amount of a mineral acid in aqueous acetone.

The principal processes described in the preceeding sections produce carboxylic acids (see Formula II). To obtain carboxy salts, the acid products are dissolved in a solvent such as ethanol, methanol, glyme, and the like, and the solution treated with an appropriate alkali or alkaline earth hydroxide or alkoxide to yield the metal salt, or with an equivalent quantity of ammonia, amine, or quarternary ammonium hydroxide to yield the amine salt. In each instance, the salt either separates from the solution and may be separated by filtration, or, when the salt is soluble, it may be recovered by evaporation of the solvent. Aqueous solutions of the carboxylic acid salts can be prepared by treating an aqueous suspension of the carboxylic acid with an equivalent amount of an alkaline earth hydroxide or oxide, alkali metal hydroxide, carbonate or bicarbonate, ammonia, an amine, or a quarternary ammonium hydroxide.

To obtain carboxy esters (i.e., compounds where R is alkoxycarbonyl), the acid products are treated in ether with an ethereal solution of the appropriate diazoalkane. For example, methyl esters are produced by reaction of the acid products with diazomethane.

To obtain carboxy hydrazides (i.e., compounds wherein R is —$CONHNH_2$), the carboxy esters of formula I where R is —$COOR^5$ and $R^2$ is restricted to hydrogen are treated, preferably in methanol or ethanol solution, with hydrazine, advantageously in the form of hydrazine hydrate. The reactions are allowed to proceed at temperatures from 25° to 55° C. and for periods of 16 to 48 hours.

To obtain the methylsulfonylamides (e.g., compounds of formula I wherein R is —$CONHSO_2CH_3$), the carboxylic acids of formula I (R=—$CO_2H$) are treated with one equivalent of methanesulfonylisocyanate and one equivalent of a base such as triethylamine in a suitable aprotic solvent, preferably acetonitrile. The reaction is conducted at 25°–50° C. and for periods of 4 to 24 hours.

To obtain the sulfoxides (compounds of formula I wherein m is 1), the compounds of formula I (wherein m is 0 and R=$CONHNH_2$ is excluded) are oxidized with sodium metaperiodate in a suitable solvent such as methanol/water. The oxidations are conducted at 0°–10° C. for periods of 12 to 48 hours.

To obtain the sulfones (compounds of formula I wherein m is 2), the compounds of formula I (wherein m is 0 and R=$CONHNH_2$ is excluded) are oxidized with a peroxy acid such as m-chloroperbenzoic acid in chloroform. The oxidations are conducted at 25°–70° C. for periods of 30 minutes to 16 hours.

To obtain the acetyl derivatives (compounds of formula I wherein $R^2$ is acetyl), the compounds of formula I wherein $R^2$ is H and R=$CONHNH_2$ is again excluded are treated with acetic anhydride in pyridine solution at temperatures of 5° to 25° C. and for periods of 2 to 5 days.

Compounds of formula I wherein Z is unsaturated (i.e., is propynylene or propenylene) may be hydrogenated over palladium or platinum catalysts to yield more highly saturated compounds of formula I. Thus, the compounds wherein Z is propynylene, may be hydrogenated to compounds where Z is cis-propenylene or, with longer reaction times, to compounds where Z is trimethylene. Similarly, compounds where Z is cis- or trans-propenylene may be hydrogenated to compounds where Z is trimethylene.

Compounds of formula I wherein $R^1$ is deuterium may be obtained from compounds of formula I wherein $R^1$ is H by dissolving the latter in deuterium oxide with an excess of sodium or potassium hydroxide and allowing the exchange reaction to proceed at 20°–30° C. for 16 to 36 hours. Workup with ordinary water removes rapidly exchangeable deuterium atoms and affords the compounds of formula I wherein $R^1$ is deuterium.

Preparation of Intermediates

I. The aldehyde intermediates III which have the following general formula:

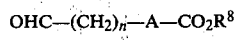

III wherein $R^8$, A, and n are as described previously, are a broad group of compounds, some of which have been described in the chemical literature. No single general method of synthesis can be prescribed for these compounds; a variety of known organic reactions can be selected for their preparation depending on the length of the chain $(CH_2)_n$ and the nature of the aromatic ring system represented by A. The following examples are chosen to illustrate the procedures that are most generally useful in the preparation of the intermediate of formula III.

(a) A synthetic scheme that is broadly applicable when n is 3 and A is p-phenylene or substituted p-phenylene is illustrated by the synthetic method used for ethyl 4-(4-oxobutyl)benzoate (XX):

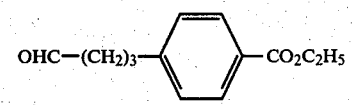

XX an aldehyde of formula III wherein $R^8$ is ethyl, A is p-phenylene, and n is 3.

In the preparation of XX, the dianion prepared by the action of lithium diisopropylamide on p-toluic acid is alkylated with 2-(2-bromoethyl)-1,3-dioxolane. The resulting 4-{3-[2-(1,3-dioxolanyl)]propyl}benzoic acid is esterified with ethyl iodide in the presence of potassium carbonate. Acid hydrolysis of the protecting cyclic acetal function gives the aldehyde intermediate XX.

(b) A synthetic method that is applicable when n is 3 or 4 and A is p-phenylene or substituted p-phenylene is illustrated by the preparative method for ethyl 4-(5-oxopentyl)benzoate (XXI):

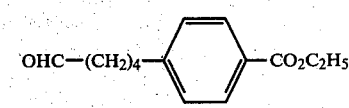

XXI

In this case, 4-bromobutylbenzene is acylated with acetyl chloride and aluminum chloride; the resulting acetophenone is oxidized with sodium hypobromite to the benzoic acid, and this compound is esterified with ethanol and mineral acid to afford ethyl 4-(4-bromobutyl)benzoate. This ester is treated with the anion prepared from methyl methylthiomethyl sulfoxide and a strong base such as sodium hydride. The resulting dimethylmercaptal S-oxide is hydrolyzed with acid catalysis to the aldehyde intermediate XXI.

The last two steps of this process are illustrated by the following scheme:

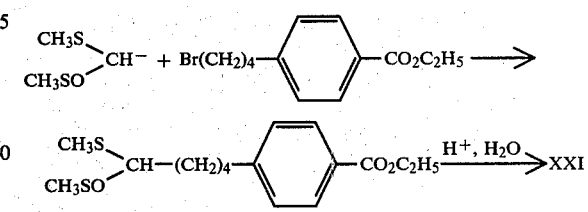

(c) A synthetic scheme that is particularly useful for preparation of aldehydes of formula III where n is 3 or 4 and A is 2,5-thienylene or 2,5-furylene is illustrated by the method of synthesis of methyl 5-(4-oxobutyl)thiophene-2-carboxylate (XXII):

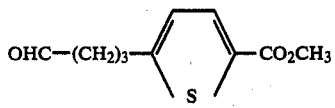

an aldehyde of formula II where A is 2,5-thienylene, n is 3, and $R^8$ is methyl. Here, the dianion prepared by the action of lithium diisopropylamide on 5-methylthiophene-2-carboxylic acid is alkylated with 3-(tetrahydro-2H-pyran-2-yloxy)propyl iodide. The product of alkylation is esterified with methyl iodide and potassium carbonate and the THP protecting group removed by acid-catalyzed hydrolysis to give methyl 5-(4-hydroxybutyl)thiophene-2-carboxylate. Oxidation of the primary alcohol functional group with chromium trioxide affords the aldehyde intermediate XXII.

(d) The synthesis of aldehydes of formula III where n is 3 and A is m-phenylene or substituted m-phenylene is illustrated by that employed for ethyl 3-(4-oxobutyl)-benzoate (XXII):

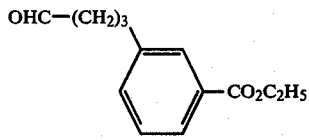

The preparation of begins with the known methyl 3-(bromomethyl)benzoate. This halide is heated in xylene solution with triphenylphosphine to yield (3-methoxycarbonylbenzyl)triphenylphosphonium bromide. The phosphonium salt is converted to the ylide with sodium ethoxide and the ylide caused to react with acetaldehyde to yield ethyl 3-(1-propenyl)benzoate. (Note that the ethyl ester has been obtained as a result of transesterification with solvent ethanol.) The ester is heated with N-bromosuccinimide in carbon tetrachloride for an extended period to yield ethyl 3-(3-bromo-1-propenyl)benzoate. This compound is treated with the anion derived from methyl methylthiomethyl sulfoxide as described in section (b) above. The resulting dimethylmercaptal S-oxide is hydrolyzed with acid catalysis to ethyl 3-(4-oxo-1-butenyl)benzoate. Hydrogenation of this olefinic aldehyde over a palladium catalyst affords the aldehyde intermediate XXIII.

II. The amine reagents of formula IV:

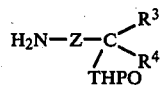

wherein $R^3$ and $R^4$ are as defined previously, THP is the tetrahydropyranyl group and Z is limited to ethylene are prepared by the following process.

Lithium diisopropylamide is made to react with acetonitrile in a suitable inert solvent such as tetrahydrofuran to give the anion $Li^+ {}^-CH_2C\equiv N$. The anion is then added to aldehydes or ketones $R^3$—CO—$R^4$. Some features of the reagents $R^3$—CO—$R^4$ should be noted. These reagents are aldehydes when $R^3$ is hydrogen. When $R^3$ is methyl and $R^3$ and $R^4$ are joined directly or through an oxygen or sulfur atom, these reagents are cyclic ketones such as cyclohexanone or tetrahydrothiopyran-4-one.

In any event, the anion addition provides alcohols of formula XXIV:

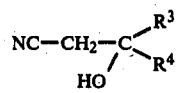

Treatment of the alcohols with dihydropyran in the presence of a suitable acid catalyst such as p-toluenesulfonic acid at room temperature gives the protected alcohols:

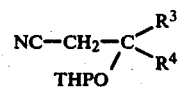

The protected alcohols are reduced with lithium aluminum hydride in a suitable inert solvent such as ether or tetrahydrofuran to afford the amine reagents IV.

If the alcohols of formula XXIV are directly reduced with lithium aluminum hydride as above, the amine reagents of formula IX are obtained:

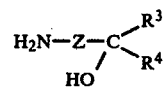

wherein $R^3$ and $R^4$ are as described previously, and Z is limited to ethylene.

An alternate procedure for preparation of amine reagents IV and IX consists of reaction of the halides of formula XIII whose preparation is described later with ammonia.

III. The halide reagents of formula XIII:

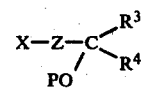

are particularly useful when Z is an unsaturated three carbon chain (propynylene or propenylene), the other groups, P, $R^3$, $R^4$, and X, being as described previously.

The process for preparation of this group of the reagents XIII begins with the reaction of lithium acetylide or ethynylmagnesium bromide with aldehydes or ketones $R^3$—CO—$R^4$ to give alcohols with the structure:

$HC\equiv C-C(OH)(R_3)(R_4)$.

These alcohols are caused to react in a variety of manners to give the reagents XIII as shown in the following scheme.

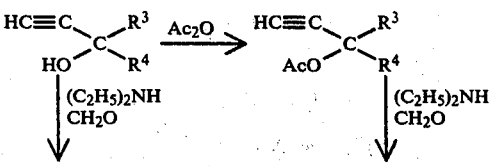

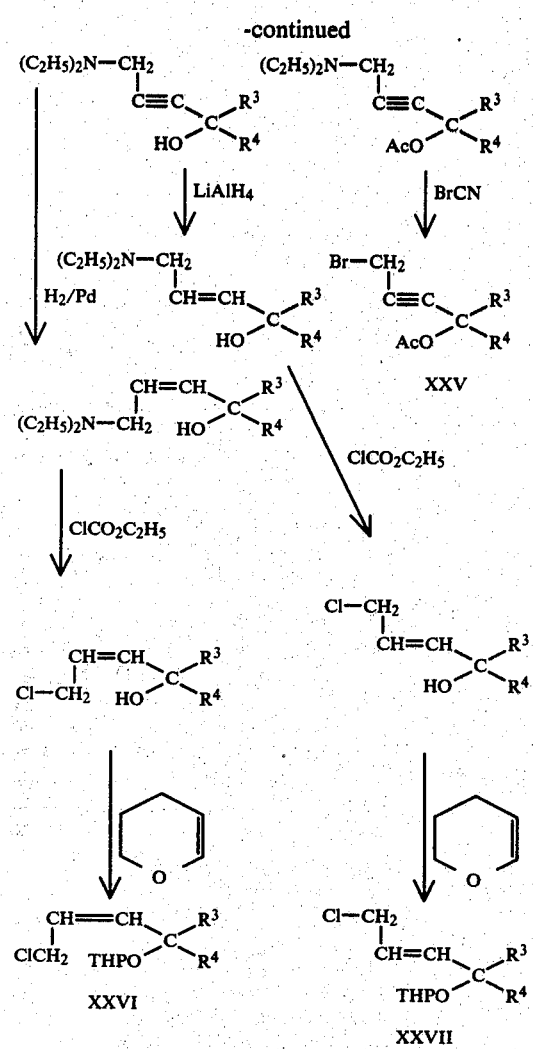
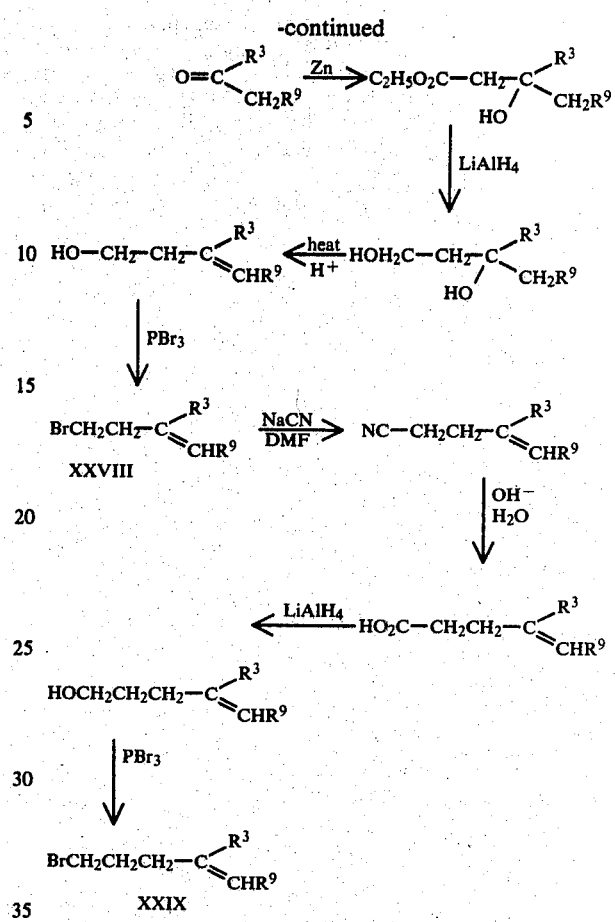

In the above scheme, the compound XXV is seen to be a halide of formula XIII where X is bromine, Z is propynylene, and P is the acetyl protecting group; compound XXVI is a halide of formula XIII where X is chlorine, Z is cis-propenylene, and P is tetrahydropyranyl; compound XXVII is a compound of formula XIII where X is chlorine, Z is trans-propenylene, and P is tetrahydropyranyl.

IV. Many halides of formula XV:

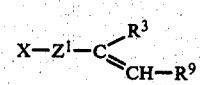

XV wherein X, $Z^1$, $R^3$, and $R^9$ are as described previously have been described in the chemical literature. These halides may be prepared by a number of different synthetic routes employing known organic reactions. Broadly applicable preparative routes for the halides XV are outlined in the following scheme.

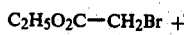 +

In the above scheme, it is seen that compound XXVIII is a halide of formula XV in which X is Br and $Z^1$ is ethylene, and compound XXIX is a halide of formula XV in which X is Br and $Z^1$ is trimethylene.

EXAMPLE 1

Preparation of 4-{3-[3-(3-Hydroxyoctyl)-4-oxo-2-thiazolidinyl]-propyl}benzoic Acid Step A: Preparation of Ethyl 4-(4-Oxobutyl)benzoate Step A-1: Preparation of Ethyl 4-{3-[2-(1,3-Dioxolanyl)]propyl}benzoate n-Butyl lithium solution (2.29 M in hexane, 35 ml., 80 mmol.) is added to a stirred solution of di-i-propylamine (8.08 g., 80 mmol.) in anhydrous THF (tetrahydrofuran, 120 ml.) and HMPA (hexamethylphosphonamide, 10 ml.) under nitrogen atmosphere. Subsequent addition of a THF (20 ml.) solution of p-toluic acid (5.44 g., 40 mmol.) results in a deep greenish-brown solution. The deep-colored solution is stirred at 0° C. for 30 minutes before being treated with a THF (10 ml.) solution of 2-(2-bromoethyl)-1,3-dioxolane. The resulting mixture is stirred for 30 minutes, and then quenched with cold water. The organic phase is separated, the aqueous layer is acidified with hydrochloric acid (2 N), and then extracted with ether. The latter ethereal extraction is washed with water, dried over anhydrous magnesium sulfate, filtered, and concentrated to give a solid residue.

The solid residue is dissolved in DMF (dimethylformamide, 50 ml.) and then successively treated with potassium carbonate (69.1 g., 50 mmol.) and ethyl iodide (9.36 g., 60 mmol.). The resulting mixture is stirred at ambient temperature for 16 hours. Additional ethyl iodide (1 g.) is added to the reaction mixture, following by heating on a steam bath for 10 minutes. The reaction mixture is then allowed to cool to room temperature, quenched with cold water, and extracted with ether. The ethereal extract is washed successively with diluted hydrochloric acid and 5% sodium bicarbonate, dried over anhydrous magnesium sulfate, filtered, and evaporated to leave an oil residue. The residue is then fractionated to give ethyl benzoate (2 g., b.p. 55°–59° C. at 0.05 mmHg.), and the desired title compound (5.81 g., 22 mmol., 55%, b.p. 135°–140° C. at 0.05 mm.), pmr (CDCl$_3$) $\delta$1.39 (3H, t, J=7 Hz), 1.76 (2H, m), 2.74 (2H, m), 3.90 (4H, m), 4.40 (2H, q, J=7 Hz), 4.89 (1H, t), 7.26 (2H, d, J=8 Hz), 8.0 (2H, d, J=8 Hz).

Step A-2: Preparation of Ethyl 4-(4-Oxobutyl)benzoate

A mixture of ethyl 4-{3-[3-(1,3-dioxolanyl)]propyl}-benzoate (0.90 g., 3.4 mmol.), water (7 ml.), acetic acid (14 ml.) plus five drops of concentrated hydrochloric acid is stirred at 50°–65° C. for 4 hours. The reaction mixture is diluted with water and extracted with ether. The ethereal extract is then washed with water twice, 5% sodium bicarbonate solution three times till neutral, dried over anhydrous magnesium sulfate, and evaporated to give the desired title compound as a pale yellow oil, pmr (CDCl$_3$) $\delta$1.40 (3H, t, J=7 Hz), 1.7~3.0 (6H, m), 4.40 (2H, q, J=7 Hz), 7.25 (2H, d, J=8 Hz), 8.0 (2H, d, J=8 Hz), 9.80 (1H, m).

Step B: Preparation of 1-Amino-3-(tetrahydro-2H-pyran-2-yloxy)octane

Step B-1: Preparation of 3-Hydroxycaprylonitrile

A 1.9 M solution (21 ml. 40 millimole) of n-butyl lithium in hexane is added cautiously to a stirred solution of freshly distilled diisopropylamine (4.04 g., 40 millimole) in anhydrous tetrahydrofuran (60 ml.) maintained at 0° C. under a nitrogen atmosphere. The resulting solution is stirred at ambient temperature for 15 minutes, cooled to −78° C., and treated with a solution of anhydrous acetonitrile (1.64 g., 40 millimole) in anhydrous tetrahydrofuran (5 ml.). The resulting turbid suspension is stirred and maintained at −78° C. for 30 minutes and then treated with a solution of hexanal (4.0 g., 40 millimole) in anhydrous tetrahydrofuran (5 ml.). After attaining a clear, yellow reaction solution, cooling at −78° C. is maintained for an additional 15 minutes. The cold reaction solution is treated with 2 N hydrochloric acid (50 ml.) and extracted with ether (100 ml.). The organic extract is washed with water (50 ml.) and 5% aqueous sodium bicarbonate (50 ml.), dried over magnesium sulfate, filtered and evaporated in vacuo, leaving the title compound as a pale yellow oil (5.2 g., 92%), pmr (CDCl$_3$) $\delta$0.97 (3H, t), 2.55 (2H, d), 3.10 (H, s) and 3.93 (H, bs).

Step B-2: Preparation of 3-(Tetrahydro-2H-pyran-2-yloxy)caprylonitrile

A mixture of 3-hydroxycaprylonitrile (5.2 g., 36.8 millimole), dihydropyran (3.8 g., 45 millimole), and p-toluenesulfonic acid.hydrate (catalytic amount) is stirred at 25° C. for 16 hours, then diluted with ether (100 ml.). The resulting solution is washed with 5% aqueous sodium hydroxide (25 ml.) and water (2×25 ml.), dried over magnesium sulfate, and filtered. Evaporation of the filtrate in vacuo affords the title compound as a pale yellow oil (7.9 g., 95%), pmr (CDCl$_3$) $\delta$0.93 (3H, t), 2.54 (2H, q) and 4.68 (H, m).

Step B-3: Preparation of 1-Amino-3-(tetrahydro-2H-pyran-2-yloxy)octane

A solution of 3-(tetrahydro-2H-pyran-2-yloxy)caprylonitrile (4.05 g., 18 millimole) in dry ether (10 ml.) is added dropwise to a stirred suspension of lithium aluminum hydride (0.76 g., 20 millimole) in dry ether (90 ml.) maintained under a nitrogen atmosphere. Upon completion of the addition, the reaction mixture is stirred and heated at reflux for 16 hours. After cooling to 25° C., the reaction mixture is treated successively with water (1 ml.), and 5% aqueous sodium hydroxide (3 ml.) added dropwise with caution, affording a fine suspension which is cooled to and maintained at 0°–5° C. for 30 minutes, and filtered. In vacuo evaporation of the solvent leaves the title compound as a pale yellow oil (3.95 g., 95%), pmr (CDCl$_3$) $\delta$0.88 (3H, t), 2.79 (2H, m) and 4.68 (H, bs).

Step C: Preparation of Ethyl 4-{3-[3-(3-Hydroxyoctyl)-4-oxo-2-thiazolidinyl]-propyl}benzoate Ethyl 4-(4-oxobutyl)benzoate (4.63 g., 21 mmol.) is added dropwise to 1-amino-3-(tetrahydro-2H-pyran-2-yloxy)octane (4.82 g., 21 mmol.) at ambient temperature. The resulting mixture is stirred for 15 minutes before adding anhydrous sodium sulfate (4 g.), and then stirred for 1 hour. The solid is subsequently removed by filtration and washed with a small quantity of benzene. The combined filtrate and washings are diluted with benzene (70 ml.) and then treated with mercaptoacetic acid (1.93 g., 21 mmol.). The resulting solution is refluxed in a Dean-Stark apparatus for 3 hours. The reaction mixture is allowed to cool to room temperature, washed successively with dilute hydrochloric acid, 5% sodium bicarbonate, dried over anhydrous magnesium sulfate, and concentrated to give an oil residue. A methanol solution (50 ml.) of the oil residue is treated with concentrated hydrochloric acid (0.2 ml.) and then stirred at ambient temperature for 16 hours. The reaction mixture is diluted with cold water, followed by extraction with ether. The ethereal extract is washed with water, 5% sodium bicarbonate, dried over anhydrous magnesium sulfate, and filtered. Evaporation of the filtrate in vacuo provides an oil residue which is then applied to a silica gel column (300 g.) with chloroform. Elution with chloroform-methanol (100:1; v:v; 1950 ml.) provides impure material; further elution with the same eluant (450 ml.) gives the title compound as a pale yellow oil (2.80 g., 6.64 mmol., 31%), pmr (CDCl$_3$) $\delta$0.90 (3H, t), 1.40 (3H, t), 3.53 (2H, s), 4.40 (2H, q), 4.70 (1H, m), 7.22 (2H, d), 8.0 (2H, d).

Step D: Preparation of 4-{3-[3-(3-Hydroxyoctyl)-4-oxo-2-thiazolidinyl]-propyl}benzoic Acid Sodium hydroxide solution (5 N, 2.5 ml., 12.5 mmol.) is added dropwise to a stirred mixture of ethyl 4-{3-[3-(hydroxyoctyl)-4-oxo-2-thiazolidinyl]propyl}benzoate (2.80 g., 6.64 mmol.) in aqueous methanol (25 ml. methanol plus 5 ml. water) maintained at 0° C. The resulting mixture is allowed to warm to room temperature and stirred for 3 hours. Then, the reaction mixture is diluted with water, and extracted with ether. The aqueous phase is separated, acidified with 2 N hydrochloric acid (10 ml.), and extracted with ether. This ethereal extract is washed with water, dried over anhydrous magnesium sulfate, concentrated in vacuo to yield an oil residue. The oil residue is then applied to a silica gel column (75 g.) with chloroform. Elution with chloroform-acetic acid (25:1; v:v; 410 ml.) gives impure material. Continued elution with the same eluant (420 ml.) provides the desired title compound as a viscous pale yellow oil, ir (NaCl) 1700, 1665 cm$^{-1}$, pmr (CDCl$_3$) δ0.92 (3H, t), 3.60 (2H, s), 4.72 (1H, m), 7.30 (2H, d), 8.08 (2H, d).

Anal. Calcd. for C$_{21}$H$_{31}$ND$_4$S: C, 64.09; H, 7.94; N, 3.56; S, 8.15. Found: C, 63.93; H, 7.70; N, 3.20; S, 8.04.

EXAMPLE 2

Preparation of 4-{3-[3-[2-(1-Hydroxycyclohexyl)ethyl]-4-oxo-2-thiazolidinyl]propyl}benzoic Acid Step A-1: Preparation of 2-(1-Hydroxycyclohexyl)acetonitrile n-Butyl lithium (1.6 M solution in n-hexane, 125 ml., 0.2 mol.) is added to a solution of di-i-propylamine (20.2 g., 0.2 mol.) in THF (280 ml.) at 0° C. under nitrogen atmosphere. The resulting mixture is then cooled to −78° C. (dry ice—isopropanol), followed by the addition of a THF (10 ml.) solution of acetonitrile (8.20 g., 0.2 mol.). The resulting mixture is stirred at −78° C. for 20 minutes, then treated with cyclohexanone (19.6 g., 0.2 mol.) and HMPA (15 ml.). Stirring is continued at −78° C. for 45 minutes before the reaction mixture is allowed to warm to room temperature. The reaction mixture is diluted with ether (100 ml.), quenched with water (200 ml.), and acidified with 3.5 N hydrochloric acid (140 ml.). The organic phase is separated, washed with water (200 ml.) and 5% sodium bicarbonate (100 ml.), dried over anhydrous magnesium sulfate, and filtered. Evaporation of the solvent in vacuo leaves the title compound as a pale yellow oil (23.6 g., 0.17 mol., 85%), pmr (CDCl$_3$) δ1.64 (8H, bs), 2.54 (2H, s), 2.64 (1H, s).

Step A-2: Preparation of 2-[1-(Tetrahydro-2H-pyran-2-yloxy)cyclohexyl]acetonitrile P-Toluenesulfonic acid hydrate (0.1 g.) is added to a stirred mixture of 2-(1-hydroxycyclohexyl)acetonitrile (5.57 g., 40 mmol.) and dihydropyran (3.78 g., 45 mmol.). As soon as the reaction is initiated (indicated by the temperature rise of the reaction mixture) the reaction vessel is quickly chilled in a cold water bath and stirring continued for 1.5 hours. The reaction mixture is then diluted with ether, washed with 5% sodium bicarbonate and dried over anhydrous magnesium sulfate. Evaporation of the solvent in vacuo provides the title compound as a yellow oil (8.70 g., 39 mmol., 98%), pmr (CDCl$_3$) δ2.63 (2H, s), 3.3~4.3 (2H, m), 4.87 (1H, m).

Step A-3: Preparation of 1-Amino-2-[1-(tetrahydro-2H-pyran-2-yloxy)cyclohexyl]ethane An ether (20 ml.) solution of 2-[1-(tetrahydro-2H-pyran-2-yloxy)cyclohexyl]acetonitrile (8.70 g., 39 mmol.) is added dropwise to a stirred suspension of lithium aluminum hydride (1.292 g., 34 mmol.) in ether (100 ml.). The resulting mixture is then refluxed for 16 hours. The reaction mixture is cooled to below 5° C., treated successively with water (1.3 ml.), 15% sodium hydroxide (1.3 ml.) and then water again (3.9 ml.). The resulting mixture is stirred at ambient temperature for 30 minutes and the precipitated solid is filtered off. The filtrate is concentrated in vacuo to yield the title compound as a pale yellow viscous oil (8.7 g., 38.2 mmol., 98%), pmr (CDCl$_3$) δ2.35 (2H, s, exchangable with D$_2$O), 2.6~3.0 (1H, m), 3.2~4.2 (3H, m), 4.74 (1H, m).

Step B: Preparation of Ethyl 4-}3-[3-[2-(1-Hydroxycyclohexyl)ethyl]-4-oxo-2-thiazolidinyl]propyl}benzoate Ethyl 4-(4-oxobutyl)benzoate (4.15 g., 18.8 mmol.) is added dropwise to a stirred solution of 1-amino-2-[1-(tetrahydro-2H-pyran-2-yloxy)cyclohexyl]ethane in carbon tetrachloride (1 ml.) maintained at 25° C. The resulting mixture is stirred for 30 minutes before being treated with anhydrous sodium sulfate (4 g.). Stirring is continued for 2 hours. The solid is removed by filtration and washed with a small quantity of benzene. The combined filtrate and washings are diluted with benzene (70 ml.), treated with HSCH$_2$CO$_2$H (1.84 g., 20 mmole.) in one portion, and then refluxed in a Dean-Stark apparatus for 16 hours. The reaction mixture is allowed to cool to room temperature, subsequently washed with diluted hydrochloric acid and 5% sodium bicarbonate, dried over anhydrous magnesium sulfate, and filtered. Evaporation in vacuo affords an oil residue which is dissolved in methanol (50 ml.) plus concentrated hydrochloric acid (0.2 ml.). The resulting mixture is stirred at ambient temperature for 3 hours, diluted with water, and extracted with ether. The ethereal extract is washed with diluted sodium bicarbonate, dried over anhydrous magnesium sulfate, filtered, and concentrated to give an oil residue. The oil residue is then applied to a silica gel column (120 g.) with chloroform. Elution with chloroform-methanol (100:1; v:v; 630 ml.) gives impure material. Further elution with the same eluant (300 ml.) provides the title compound (2.5 g., 5.96 mmol., 32%) as a pale yellow oil, pmr (CDCl$_3$) δ1.38 (3H, t), 3.50 (2H, s), 4.40 (2H, q), 4.72 (1H, m), 7.23 (2H, d), 8.00 (2H, d).

Step C: Preparation of 4-{3-[3-[2-(1-Hydroxycyclohexyl)-ethyl]-4-oxo-2-thiazolidinyl]propyl}benzoic Acid Sodium hydroxide solution (5 N, 2.5 ml., 12.5 mmol.) is added to a stirred mixture of ethyl 4-{3-[3-[2-(1-hydroxycyclohexyl)ethyl]-4-oxo-2-thiazolidinyl]propyl}benzoate (2.48 g., 5.91 mmol.), methanol (25 ml.) and water (5 ml.). The resulting mixture is stirred at ambient temperature for 16 hours. Then, it is diluted with water, acidified with diluted hydrochloric acid, and extracted with ether. The ethereal extract is washed with water, dried over anhydrous magnesium sulfate, and filtered. Upon cooling the filtrate, the title compound precipitates out as a white solid, which is collected by filtration (7.06 g., 2.57 mmol., 42%). The product is recrystallized from chloroform-ether, m.p. 147°–148° C., ir (KBr) 3320, 1700, 1650 cm$^{-1}$, pmr (CDCl$_3$) δ3.54 (2H, s), 4.70 (1H, m), 7.22 (2H, d), 8.00 (2H, d).

Anal. Calcd. for C$_{21}$H$_{29}$NO$_4$S: C, 64.42; H, 7.47; N, 3.58. Found: C, 63.97; H, 7.23; N, 3.40.

EXAMPLE 3

Formulations of 4-{3-[3-[2-(1-Hydroxycyclohexyl)ethyl]-4-oxo-2-thiazolidinyl]propyl}benzoic Acid A. Capsule Formulation

| | |
|---|---|
| 4-{3-[3-[2-(1-Hydroxycyclohexyl)ethyl]-4-oxo-2-thiazolidinyl]propyl}benzoic acid | 10 g. |
| Stearic acid (U.S.P. triple pressure) | 125 g. |
| Pluronic F-68 | 7.5 g. |
| Corn Starch | 125 g. |

The stearic acid and pluronic are united in a vessel and melted using a water bath at 60° to 65° C. The heating is discontinued and the 4-{3-[3-[2-(1-hydroxycyclohexyl)ethyl]-4-oxo-2-thiazolidinyl]propyl}benzoic acid is dispersed into the mixture and the corn starch is added with stirring which is continued until the mixture cools to ambient temperature. The mixture is reduced to granules by screening and placed in a number 0 hard gelatin containing 267.5 mg. of total solids and 10 mg. of 4-{3-[3-[2-(1-hydroxycyclohexyl)ethyl]-4-oxo-2-thiazolidinyl]-propyl}benzoic acid per capsule.

B. Parenteral Formulation of the Multidose Solution for Intramuscular and Intravenous Use

| | |
|---|---|
| 4-{3-[3-[2-(1-Hydroxycyclohexyl)ethyl]-4-oxo-2-thiazolidinyl]propyl}benzoic acid | 1 g. |
| Tris-(hydroxymethyl)aminomethane (Reagent Grade THAM) | q.s. to adjust solution to pH 7.4 |
| Sodium Chloride (U.S.P.) | q.s. to yield isotonic solution |
| Methylparaben | 10 mg. |
| Polyparaben | 1 mg. |
| Distilled water (pyrogen-free) | q.s. to 10 ml. |

The 4-{3-[3-[2-(1-Hydroxycyclohexyl)ethyl]-4-oxo-2-thiazolidinyl]propyl}benzoic acid suspended in about 6 ml. of the water is treated with tris-(hydroxymethyl)aminomethane with stirring until the pH reaches 7.4. The methylparaben and propylparaben are added with stirring and sufficient sodium chloride is added to produce an isotonic solution. After water is added to bring the final volume to 10 ml., the solution is sterilized by membrane filtration and placed in a vial by an aseptic technique. The solution contains the THAM salt of 4-{3-[3-[2-(1-hydroxycyclohexyl)ethyl]-4-oxo-2-thiazolidinyl]propyl}benzoic acid equivalent to 100 mg./ml. of the free acid.

C. Preparation of Suppositories

| | |
|---|---|
| 4-{3-[3-[2-(1-Hydroxycyclohexyl)ethyl]-4-oxo-2-thiazolidinyl]propyl}benzoic acid | 200 g. |
| Butylated hydroxyanisole | 82 mg. |
| Butylated hydroxytoluene | 82 mg. |
| Ethylenediamine tetraacetic acid | 163 mg. |
| Glycerine, U.S.P. | 128 g. |
| Sodium chloride, microfine | 52.5 g. |
| Polyethylene glycol 6000 | 128 g. |
| Polyethylene glycol 4000 | 1269 g. |

The polyethylene glycol 4000 and polyethylene glycol 6000 are placed in a vessel surrounded by a water bath at such a temperature as required to maintain the melted contents at 60° to 65° C. To the melt is added the butylated hydroxyanisole and butylated hydroxytoluene with stirring. Then the ethylenediamine tetraacetic acid and microfine sodium chloride are added to and dispersed in the mixture. The 4-{3-[3-[2-(1-Hydroxycyclohexyl)ethyl]-4-oxo-2-thiazolidinyl]propyl}benzoic acid is then added and dispersed into the mixture. Finally, the temperature is lowered to 55° to 60° C. and the glycerine is added and dispersed.

While maintaining the temperature of 55° to 60° C. and continuous mixing, the melt is dispersed into plastic suppository cavities of a conventional suppository cold-molding device. The suppositories thus prepared contain a total of 1.7778 g. of contents of which 200 mg. are 4-{3-[3-[2-(1-Hydroxycyclohexyl)ethyl]-4-oxo-2-thiazolidinyl]propyl}benzoic acid.

EXAMPLE 4

Preparation of 4-{3-[3-[2-(1-Hydroxycyclohexyl)ethyl]-4-oxo-2-thiazolidinyl]propyl}benzoic Acid (Alternate Method)

Step A: Preparation of Ethyl 4-[3-(4-oxo-2-thiazolidinyl)propyl]benzoate

A mixture of ethyl 4-(4-oxobutyl)benzoate (24.89 g., 0.113 mole), mercaptoacetamide (30.93 g., 0.339 mole), p-toluenesulfonic acid monohydrate (250 mg.), and benzene (290 ml.) is heated, under $N_2$, under reflux employing a Dean-Stark constant water separator for two hours.

The cooled reaction mixture is poured into water (600 ml.) and the resulting oil is extracted into ether. The combined extracts are washed well with water and dried over anhydrous magnesium sulfate. The solvent is removed under vacuum to give the title compound as a yellow solid. After triturating with cyclohexane (75 ml.), there is obtained 19.70 g., m.p. 97°–99° C. of white solid. Recrystallization from butyl chloride gives white needles, m.p. 99°–100° C.

Anal. Calc'd for $C_{15}H_{19}NO_3S$: C, 61.41; H, 6.53; N, 4.77. Found: C, 61.32; H, 6.55; N, 4.77.

Step B: Preparation of Ethyl 4-{3-[3-(2-(1-Cyclohexenyl)ethyl)-4-oxo-2-thiazolidinyl]propyl}benzoate Ethyl 4-[3-(4-oxo-2-thiazolidinyl)propyl]benzoate (14.67 g., 0.05 mole) is dissolved in 35 ml. of 1:1 benzene-DMF and the solution is added dropwise during 30 minutes to a suspension of sodium hydride (1.3 g., 0.055 mole) in 50 ml. of 1:1 benzene-DMF. Temperature is held at 30° C. during the addition by means of a cold water bath. The mixture is stirred for an additional 15 minutes and then treated during 15 minutes with 1-(2-bromoethyl)cyclohexene (10.4 g., 0.055 mole). The mixture is then stirred and heated at 55°–60° C. for 3.5 hours. The mixture is cooled and poured into 200 ml. of water. The product is taken up in ether, washed with water, and dried over $MgSO_4$. Evaporation of solvent at reduced pressure gives 20.5 g. of crude product as an orange viscous oil.

The crude product is chromatographed on a column containing 300 g. of silica gel; elution is with chloroform followed by 2% methanol in chloroform. Fractions are combined and evaporated to give two product fractions: (A) 4.5 g. yellow oil $R_f$ 0.60 with minor impurities at $R_f$ 0.42 and 0.78 (tlc on $SiO_2$ with 2% methanol in chloroform; and (B) 7.8 g., yellow oil, one spot, $R_f$ 0.60. The combined yield of product used in the next step is 12.3 g. (61%).

Anal. Calc'd for $C_{23}H_3NO_3S$: C, 68.79; H, 7.78; N, 3.49. Found: C, 68.52; H, 7.68; N, 3.37.

Step C: Preparation of 4-{3-[3-(2-(1-Hydroxycyclohexyl)ethyl)-4-oxo-2-thiazolidinyl]propyl}benzoic Acid A solution of the product of Step B above (3.6 g., 0.009 mole) in trifluoroacetic acid (16 ml.) is allowed to stand for 4 hours at room temperature. The solution is then poured into ice-water. The oily product is taken up in ether and the solution washed with saturated $NaHCO_3$ solution until the washings remain basic. At the point when excess $CF_3CO_2H$ has been completely removed, the oily product separates from the ether solution. It is redissolved in the organic phase by addition of chloroform. The organic solution is then washed with water and dried over Na$_2$SO$_4$. Evaporation of solvents affords 4.3 g. of residual brown oil.

This product is dissolved in a solution of sodium hydroxide (1.2 g., 0.03 mole) in water (10 ml.) and methanol (40 ml.). The solution is allowed to stand at room temperature for 18 hours. The methanol is distilled at reduced pressure. The residual solution is diluted with 50 ml. of water and acidified with concentrated hydrochloric acid. The product precipitates as an oil which quickly crystallizes. It is recrystallized twice to constant melting point from acetonitrile-water. There is obtained 1.6 g. (45%) of 4-{3-[3-(2-(1-hydroxycyclohexyl)ethyl)-4-oxo-2-thiazolidinyl]propyl}benzoic acid, m.p. 147°-148° C.

EXAMPLE 5

Preparation of
4-{3-[3-[2-(1-Hydroxycyclohexyl)ethyl]-4-oxo-2-thiazolidinyl]propyl}benzoic Acid (Alternate Method)

Step A: Preparation of
4-{3-[3-[2-(1-Cyclohexenyl)ethyl]-4-oxo-2-thiazolidinyl]propyl}benzoic Acid A solution of ethyl 4-{3-[3-[2-(1-cyclohexenyl)ethyl]-4-oxo-2-thiazolidinyl]propyl}benzoate (Example 4, Step B) (4.0 g., 0.01 mole) and sodium hydroxide (1.2 g., 0.003 mole) in methanol (50 ml.) and water (5 ml.) is allowed to stand at 25° C. for 18 hours. The methanol is distilled at reduced pressure. The residual solution is treated with water (50 ml.) and acidified with 2 N hydrochloric acid. The title compound precipitates as an oil that gradually crystallizes. It is collected, washed with water, and air dried.

Step B: Preparation of
4-{3-[3-[2-(1-Hydroxycyclohexyl)ethyl]-4-oxo-2-thiazolidinyl]propyl}benzoic Acid A solution of 4-{3-[3-[2-(1-Cyclohexenyl)ethyl]-4-oxo-2-thiazolidinyl]propyl}benzoic acid (3.7 g., 0.01 mole) in trifluoroacetic acid (20 ml.) is allowed to stand at 25° C. for 4 hours. Excess trifluoroacetic acid is then removed by evaporation at reduced pressure. The oily residue is dissolved in a solution of sodium hydroxide (2.0 g., 0.05 mole) in water (40 ml.). The basic solution is acidified with 2 N hydrochloric acid. The title compound precipitates as a solid. Recrystallization from acetonitrile-water yields the purified title compound, m.p. 147°-148° C.

EXAMPLE 6

Preparation of
4-{3-[3-[2-(1-Hydroxycyclohexyl)ethyl]-1,4-dioxo-2-thiazolidinyl]propyl}benzoic Acid Sodium metaperiodate (0.75 g., 3.5 mmoles) is added to a cold (0°-5° C.) solution of 4-{3-[3-[2-(1-hydroxycyclohexyl)ethyl]-4-oxo-2-thiazolidinyl]propyl}benzoic acid (1.33 g., 3.4 mmoles) in methanol (20 ml.) and water (5 ml.). The resulting mixture is stirred without further cooling for 16 hours. The precipitated solid is then removed by filtration. The filtrate is diluted with water and extracted with chloroform. The organic extract is washed with brine, dried over sodium sulfate, and evaporated in vacuo to leave an oily residue which is chromatographed on silica gel (25 g.). Elution with 4% acetic acid in chloroform affords the title compound as a viscous, yellowish oil.

EXAMPLE 7

Preparation of
4-{3-[3-[2-(1-Hydroxycyclohexyl)ethyl]-1,1,4-trioxo-2-thiazolidinyl]propyl}benzoic Acid A mixture of 4-{3-[3-[2-(1-hydroxycyclohexyl)ethyl]-4-oxo-2-thiazolidinyl]propyl}benzoic acid (0.391 g., 1.0 mmol.), m-chloroperoxybenzoic acid (100%, 0.362 g., 2.1 mmol.), and chloroform (5 ml.) is refluxed for 30 minutes. The reaction mixture is evaporated in vacuo to give a solid residue which is applied to a silica gel column (18 g.) with chloroform. Elution with chloroform-acetic acid (25:1; v:v; 150 ml.) provides m-chlorobenzoic acid and impure material. Continued elution with the same eluant affords the title compound as a colorless viscous oil (0.273 g., 0.64 mmol., 64%), pmr (CDCl$_3$) δ 3.75 (2H, s), 4.60 (1H, m), 7.26 (2H, d), 8.00 (2H, d).

EXAMPLE 8

Preparation of
4-{3-[3-[2-(1-Hydroxycyclohexyl)ethyl]-4-oxo-2-thiazolidinyl]propyl}-3-chlorobenzoic Acid Step A: Preparation of Ethyl
3-Chloro-4-(4-oxobutyl)benzoate This compound is prepared by the same series of reactions described in Example 1, Step A, for the preparation of ethyl 4-(4-oxobutyl)benzoate, except that in Step A-1, 3-chloro-4-methylbenzoic acid is substituted for p-toluic acid. There is thus obtained in Step A-1 of this example, ethyl 3-chloro-4-{3-[2-(1,3-dioxolanyl)]-propyl}benzoate, b.p. 175°-178° C. (0.2 mm.); and in Step A-2, ethyl 3-chloro-4-(4-oxobutyl)benzoate.

Step B: Preparation of Ethyl
4-{3-[3-[2-(1-Hydroxycyclohexyl)ethyl]-4-oxo-2-thiazolidinyl]propyl}-3-chlorobenzoate This compound is prepared by the method described in Example 2, Step B, except that an equivalent quantity of ethyl 3-chloro-4-(4-oxobutyl)benzoate is substituted for the ethyl 4-(4-oxobutyl)benzoate of Example 2, Step B. The title compound is obtained as a viscous, brownish oil.

Step C: Preparation of
4-{3-[3-[2-(1-Hydroxycyclohexyl)ethyl]-4-oxo-2-thiazolidinyl]propyl}-3-chlorobenzoic Acid The hydrolysis of the ester product of Step B above is carried out exactly analogously to the hydrolysis described in Example 2, Step C. The title compound after chromatography on silica gel with 2% methanol in chloroform elution is obtained as an extremely viscous, yellowish oil.

EXAMPLE 9

Preparation of
4-{3-[3-[2-(1-Hydroxycyclohexyl)ethyl]-4-oxo-2-thiazolidinyl]propyl}-2-chlorobenzoic Acid Step A: Preparation of Ethyl
2-chloro-4-(4-oxobutyl)benzoate This compound is prepared by the same series of reactions described in Example 1, Step A, for the preparation of ethyl 4-(4-oxobutyl)benzoate except that, in Step A-1, 2-chloro-4-methylbenzoic acid is substituted for p-toluic acid. There is thus obtained in Step A-1 of this example, ethyl 2-chloro-4-{3-[2-(1,3-dioxolanyl)]- propyl}benzoate, b.p. 165°–170° C. (0.1 mm.), and in Step A-2, ethyl 2-chloro-4-(4-oxobutyl)benzoate.

Step B: Preparation of Ethyl 3-Chloro-4-[3-(4-oxo-2-thiazolidinyl)propyl]benzoate This compound is prepared by the method described in Example 4, Step A, except that an equivalent quantity of ethyl 2-chloro-4-(4-oxobutyl)benzoate is substituted for the ethyl 4-(4-oxobutyl)benzoate of Example 4, Step A. The title compound is obtained as white needles (from butyl chloride), m.p. 81.5°–82.5° C.

Anal. Calc'd for $C_{15}H_{18}ClNO_3S$: C, 54.96; H, 5.53; N, 4.27. Found: C, 55.29; H, 5.64; N, 4.31.

Step C: Preparation of Ethyl 2-Chloro-4-{3-[3-[2-(1-Cyclohexenyl)ethyl]-4-oxo-2-thiazolidinyl]propyl}benzoate This compound is prepared by the method described in Example 4, Step B, except that an equivalent quantity of ethyl 2-chloro-4-[3-(4-oxo-2-thiazolidinyl)propyl]benzoate is substituted for the ethyl 4-[3-(4-oxo-2-thiazolidinyl)propyl]benzoate of Example 4, Step B. The title compound is obtained as an oil by column chromatography on silica gel with 2% methanol in chloroform as eluant.

Step D: Preparation of 4-{3-[3-[2-(1-Hydroxycyclohexyl)ethyl]-4-oxo-2-thiazolidinyl]propyl}-2-chlorobenzoic Acid This compound is prepared by the method described in Example 4, Step C, except that an equivalent quantity of ethyl 2-chloro-4-{3-[3-[2-(1-cyclohexenyl)ethyl]-4-oxo-2-thiazolidinyl]propyl}benzoate is substituted for the ester employed in Example 4, Step B. The title compound is obtained as an amorphous solid, m.p. 104°–108° C.

Anal. Calc'd for $C_{21}H_{28}ClNO_4S$: C,59.21; H,6.63; N,3.29. Found: C,59.00; H,6.52; N,3.23.

EXAMPLE 10

Preparation of 4-{3-[3-[2-(1-Hydroxycyclohexyl)ethyl]-4-oxo-2-thiazolidinyl]propyl}-3-methylbenzoic Acid Step A: Preparation of Ethyl 3-Methyl-4-(4-oxobutyl)benzoate This compound is prepared by the same series of reactions described in Example 1, Step A, for the preparation of ethyl 4-(4-oxobutyl)benzoate except that in Step A-1, 3,4-dimethylbenzoic acid is substituted for p-toluic acid. There is thus obtained in Step A-1 of this example, ethyl 3-methyl-4-{3-[2-(1,3-dioxolanyl)]propyl}benzoate, and in Step A-2, ethyl 3-methyl-4-(4-oxobutyl)benzoate.

Step B: Preparation of Ethyl 4-{3-[3-[2-(1-Hydroxycyclohexyl)ethyl]-4-oxo-2-thiazolidinyl]propyl}-3-methylbenzoate This compound is prepared by the method described in Example 2, Step B, except that an equivalent quantity of ethyl 3-methyl-4-(4-oxobutyl)benzoate is substituted for the ethyl 4-(4-oxobutyl)benzoate of Example 2, Step B. The title compound is obtained as a viscous, yellow oil.

Step C: Preparation of 4-{3-[3-[2-(1-Hydroxycyclohexyl)ethyl]-4-oxo-2-thiazolidinyl]propyl}-3-methylbenzoic Acid The hydrolysis of the ester product of Step B above is carried out exactly analogously to the hydrolysis described in Example 2, Step C. The title compound, after chromatography on silica gel with 2% methanol in chloroform elution, is obtained as an extremely viscous, yellow oil.

EXAMPLE 11

Preparation of 4-{4-[3-[2-(1-Hydroxycyclohexyl)ethyl]-4-oxo-2-thiazolidinyl]butyl}benzoic Acid Step A-1: Preparation of 4-(4-Bromobutyl)acetophenone A suspension of aluminum chloride (84 g., 0.63 mole) in a mixture of acetyl chloride (45 ml.) and carbon disulfide (300 ml.) is cooled in an ice bath and treated dropwise during 30 minutes with a mixture of 4-phenylbutyl bromide (128 g., 0.6 mole) and acetyl chloride (93 ml.). At the end of the addition, the temperature is 5°–10° C. The cooling bath is removed and stirring is continued for 2 hours.

The reaction mixture is poured in finely ground ice (600 g.) and concentrated hydrochloric acid (60 ml.). The resulting oil is taken up in ether, washed with water, and dried over sodium sulfate. Solvents are evaporated, and the residual oil distilled at reduced pressure (14 mm.) to yield the title compound as a light yellow oil.

Step A-2: Preparation of 4-(4-Bromobutyl)benzoic Acid

A solution of sodium hydroxide (163.7 g., 4.092 moles) in water (1400 ml.) and dioxane (1000 ml.) is cooled to 15° C. and treated during 30 minutes with bromine (238.10 g., 1.488 moles) at 10°–15° C. Then 4-(4-bromobutyl)acetophenone (127 g., 0.496 mole) is added during 1 hour at 5°–10° C. Stirring is continued until the hypobromite is exhausted (about 2 hours).

The reaction solution is acidified with concentrated hydrochloric acid. The supernatant is decanted from a semi-solid which separates. This material is dissolved in ether, washed with water, and dried over magnesium sulfate. Evaporation of ether in vacuo affords the title acid which is purified by recrystallization from benzene and petroleum ether.

Step A-3: Preparation of Ethyl 4-(4-Bromobutyl)benzoate

A mixture of 4-(4-bromobutyl)benzoic acid (105.5 g., 0.41 mole), benzene (290 ml.), ethanol (60 ml.), and concentrated sulfuric acid (1.5 ml.) is heated at reflux under a Dean-Stark water separator until the evolution of water ceases (approximately 24 hours).

The cooled reaction solution is washed with water and dried over magnesium sulfate. The solvents are evaporated in vacuo, and the residual oil distilled at reduced pressure (0.1 mm.) to yield the title compound as a colorless, moderately viscous oil.

Step A-4: Preparation of Ethyl 4-(5-Oxopentyl)benzoate

Methyl methylthiomethyl sulfoxide (12.4 g., 0.1 mole) is added dropwise during 30 minutes to a stirred suspension of sodium hydride (2.4 g., 0.1 mole) in tetrahydrofuran (100 ml.). Then, ethyl 4-(4-bromobutyl)benzoate (28.5 g., 0.1 mole) is added in one portion, and the mixture is stirred at 30° C. for 2 hours and at 45°–50° C.

for 18 hours. The solvent is evaporated in vacuo. The residue is treated with water, and the oily product is taken up in ether and dried over sodium sulfate. Evaporation of the ether affords the dimethyl mercaptal S-oxide of the title aldehyde. This material is dissolved in 200 ml. of tetrahydrofuran with 5 ml. of 10% hydrochloric acid, and the solution refluxed 3 hours. The solvent is evaporated, and the residue is taken up in ether, washed with water, and dried over sodium sulfate. Evaporation of the solvent in vacuo affords the title aldehyde as a mobile oil.

Step B: Preparation of Ethyl 4-{4-[3-[2-(1-Hydroxycyclohexyl)ethyl]-4-oxo-2-thiazolidinyl]butyl}benzoate This compound is prepared by the method described in Example 2, Step B, except that an equivalent quantity of ethyl 4-(5-oxopentyl)benzoate is substituted for ethyl 4-(4-oxobutyl)benzoate. The title compound is obtained as a viscous, yellow oil.

Step C: Preparation of 4-{4-[3-[2-(1-Hydroxycyclohexyl)ethyl]-4-oxo-2-thiazolidinyl]butyl}benzoic Acid This compound is prepared by the method described in Example 2, Step C, except that an equivalent quantity of the ester of Step B above is subjected to hydrolysis. The title compound is purified by column chromatography on silica gel with 2% methanol in chloroform elution. It is obtained as a viscous, yellowish oil.

EXAMPLE 12

Preparation of 3-{3-[3-[2-(1-Hydroxycyclohexyl)ethyl]-4-oxo-2-thiazolidinyl]propyl}benzoic Acid Step A-1: Preparation of Ethyl 3-(1-Propenyl)benzoate (3-Methoxycarbonylbenzyl)triphenylphosphonium bromide (54.1 g., 0.11 mole) is suspended with stirring in a mixture of acetaldehyde (5.8 g., 0.132 mole) and ethanol (250 ml.). A solution of sodium (2.5 g., 0.11 mole) in ethanol (300 ml.) is added dropwise during 30 minutes. The reaction mixture is stirred an additional 4 hours at room temperature and then concentrated to about ¼ volume at reduced pressure. Water (150 ml.) is added to the residue, and the oily product taken up in ether and dried over magnesium sulfate. Ether is evaporated. The residue is treated with 100 ml. of petroleum ether. Insoluble triphenylphosphine oxide is filtered off, and the filtrate distilled in vacuo to yield 14.0 g. (72%) of ethyl 3-(1-propenyl)benzoate, b.p. 85°–87° C. (0.1 mm.). Note that the product is an ethyl ester as a result of transesterification with solvent ethanol during the reaction.

Step A-2: Preparation of Ethyl 3-(3-Bromo-1-propenyl)benzoate

A mixture of ethyl 3-(1-propenyl)benzoate (14.0 g., 0.074 mole), N-bromosuccinimide (14.9 g., 0.084 mole), benzoyl peroxide (150 mg.), and carbon tetrachloride (75 ml.) is stirred and heated at reflux for 46 hours. The mixture is cooled. Solids are filtered off, and the filtrate is washed with water and dried over magnesium sulfate. The solvent is evaporated, and the residual oil distilled to yield 10.2 g. (51%) of ethyl 3-(3-bromo-1-propenyl)benzoate, b.p. 129°–131° C. (0.05 mm.).

Step A-3: Preparation of Ethyl 3-(4-Oxo-1-butenyl)benzoate

Methyl methylthiomethyl sulfoxide (12.4 g., 0.1 mole) is added dropwise during 30 minutes to a stirred suspension of sodium hydride (2.4 g., 0.1 mole) in tetrahydrofuran (100 ml.). Then, ethyl 3-(3-bromo-1-propenyl)benzoate (26.9 g., 0.1 mole) is added in one portion, and the mixture is stirred at 30° C. for 2 hours and at 45°–50° C. for 2 hours. The solvent is evaporated in vacuo. The residue is treated with water, and the oily product is taken up in ether and dried over sodium sulfate. Evaporation of the ether affords the dimethyl mercaptal S-oxide of the title aldehyde. This material is dissolved in 200 ml. of tetrahydrofuran with 5 ml. of 10% hydrochloric acid and the resulting solution is refluxed for 2 hours. The solvent is evaporated, and the residue is taken up in ether, washed with water, and dried over sodium sulfate. Evaporation of the solvent in vacuo affords the title aldehyde as a mobile oil which is used immediately in the next step.

Step B: Preparation of Ethyl 3-{3-[3-[2-(1-Hydroxycyclohexyl)ethyl]-4-oxo-2-thiazolidinyl]propenyl}benzoate This compound is prepared by the method described in Example 2, Step B, except that an equivalent amount of ethyl 3-(4-oxo-1-butenyl)benzoate is substituted for ethyl 4-(4-oxobutyl)benzoate. The title compound is obtained as a viscous, yellow oil.

Step C: Preparation of 3-{3-[3-[2-(1-Hydroxycyclohexyl)ethyl]-4-oxo-2-thiazolidinyl]propenyl}benzoic Acid This compound is prepared by the method described in Example 2, Step C, except that an equivalent quantity of the ester obtained in Step B is subjected to hydrolysis. The title compound is obtained as a viscous, yellow oil after purification by chromatography on silica gel with 2% methanol in chloroform elution.

Step D: Preparation of 3-{3-[3-[2-(1-Hydroxycyclohexyl)ethyl]-4-oxo-2-thiazolidinyl]propyl}benzoic Acid 3-{3-[3-[2-(1-Hydroxycyclohexyl)ethyl]-4-oxo-2-thiazolidinyl]propenyl}benzoic acid (7.8 g., 0.02 mole) in ethanol (125 ml.) is hydrogenated over 2.5 g. of a 5% Pd on charcoal catalyst at 1 atmosphere pressure and 27° C. When the theoretical amount (0.02 mole) of hydrogen has been absorbed, the catalyst is filtered off, the solvent evaporated, and the residue chromatographed on silica gel with 4% methanol in chloroform as the eluant. The title compound is obtained as a colorless, viscous oil.

EXAMPLE 13

Preparation of 5-{3-[3-[2-(1-Hydroxycyclohexyl)ethyl]-4-oxo-2-thiazolidinyl]propyl}thiophene-2-carboxylic Acid Step A: Preparation of Methyl 5-(4-Oxobutyl)thiophene-2-carboxylate Step A-1: Preparation of Methyl 5-[4-(Tetrahydro-2H-pyran-2-yloxy)butyl]thiophene-2-carboxylate A solution of butyllithium (2.25 M in hexane, 44.4 ml., 0.1 mole) is added to a solution of diisopropylamine (10.1 g., 0.1 mole) in tetrahydrofuran (95 ml.) at −5° C. The solution is stirred at −5° C. for 0.5 hours and then treated with a solution of 5-methylthiophene-2-carboxylic acid (7.11 g., 0.05 mole) in tetrahydrofuran (10 ml.). This solution is stirred at 0° C. for one hour and then 3-(tetrahydro-2H-pyran-2-yloxy)propyl iodide (13.5 g., 0.05 mole) is added. The resulting solution is allowed to stand without further cooling for 18 hours. It is then poured onto ice. The mixture is acidified with 2 N hydrochloric acid and extracted with methylene chloride. The extracts are dried over magnesium sulfate and evaporated to give a residue weighing 14.7 g.

A mixture of this material, methyl iodide (11.0 g., 0.078 mole), potassium carbonate (8.9 g., 0.065 mole) and dimethylformamide (40 ml.) is stirred at 25° C. for 2 days. The mixture is poured into water. The product is taken up in ether and dried over magnesium sulfate. Evaporation of the solvent leaves 14.2 g. (47%) of the title compound as a yellowish oil.

Step A-2: Preparation of Methyl 5-(4-Hydroxybutyl)-thiophene-2-carboxylate

A solution of methyl 5-[4-tetrahydro-2H-pyran-2-yloxy)butyl]thiophene-2-carboxylate (10.6 g., 0.036 mole), and pyridinium p-toluenesulfonate (1.0 g., 0.004 mole) in methanol (20 ml.) is heated at 75° C. for 10 hours. The solution is diluted with ether, filtered, washed with water, dried over magnesium sulfate, and distilled to afford 4.72 g. (16%) of the title ester, b.p. 147°-164° C. (0.1 mm.).

Anal. Calc'd for $C_{10}H_{14}O_3S$: C, 56.05; H, 6.58; S, 14.97. Found: C, 56.37; H, 6.78; S, 14.69.

Step A-3: Preparation of Methyl 5-(4-Oxobutyl)thiophene-2-carboxylate

A solution of the ester product of Step A-2 (5.92 g., 0.028 mole) in methylene chloride (5 ml.) is added with stirring to a solution of chromium trioxide (16.8 g., 0.168 mole) in pyridine (26.58 g., 0.336 mole) and methylene chloride (100 ml.). The resulting mixture is stirred for 2 hours at 25°-30° C. The methylene chloride solution is decanted from solids, washed with dilute hydrochloric acid and water, and dried over magnesium sulfate. The solution is then evaporated. The residue is triturated with ether. The ether extract is filtered, washed with sodium bicarbonate solution and water, dried ($MgSO_4$) and concentrated to yield 2.9 g. of the title aldehyde as a greenish oil.

Step B: Preparation of 1-(2-Aminoethyl)cyclohexanol

A mechanically stirred suspension of lithium tetrahydridoaluminate (8.52 g., 0.2245 mole) in ether (200 ml.), under $N_2$, is treated with a solution of 2-(1-hydroxycyclohexyl)acetonitrile (25.00 g., 0.1796 mole) in ether (60 ml.), dropwise, during one hour. Refluxing and stirring is continued for 2½ hours, and then the mixture is stirred at 25° C. for 16 hours.

The mixture is cooled in an ice bath and treated cautiously and successively with water (8.5 ml.), 15 % aqueous sodium hydroxide solution (8.5 ml.) and water (25.6 ml.). The cooling bath is removed and stirring is continued for 30 minutes. The white precipitate is removed by filtration and washed well with ether. The combined filtrate and washings are dried over anhydrous sodium sulfate. The solvent is removed under vacuum and the residual oil is distilled to give the title compound as a colorless oil, yield 13.28 g. (52%), b.p. 85°-87° C./0.25 mm.

Step C: Preparation of Methyl 5-{3-[3-[2-(1-Hydroxycyclohexyl)ethyl]-4-oxo-2-thiazolidinyl]propyl}thiophene-2-carboxylate Methyl 5-(4-oxobutyl)thiophene-2-carboxylate (161.0 g., 0.76 mole) is added dropwise during 20 minutes to a stirred solution of 1-(2-aminoethyl)cyclohexanol (129.5 g., 0.91 mole) in toluene (500 ml.). The mixture is stirred at 30° C. for 30 minutes and then refluxed under a Dean-Stark water separator for 30 minutes until the formed water is removed. Toluene (500 ml.), methyl thioglycollate (118.7 g., 1.12 mole), and triethylamine (30 ml.) are then added. The solution is boiled under reflux for 21 hours. It is then cooled, washed with 2 N hydrochloric acid and water and dried over sodium sulfate. Evaporation of the solvent gives the title product as a viscous orange oil weighing 339 g.

Step D: Preparation of 5-{3-[3-[2-(1-Hydroxycyclohexyl)ethyl]-4-oxo-2-thiazolidinyl]propyl}thiophene-2-carboxylic Acid This compound is prepared by the hydrolytic method described in Example 2, Step C, except that an equivalent quantity of the ester product of Step B above is substituted for the ester submitted to hydrolysis in Example 2, Step C. The title compound has m.p. 122°-123° C.

Anal. Calc'd for $C_{19}H_{27}NO_4S_2$: C, 57.40; H, 6.85; N, 3.52. Found: C, 57.41; H, 6.93; N, 3.66.

EXAMPLE 14

Preparation of 5-{3-[3-[2-(1-Hydroxycyclohexyl)ethyl]-4-oxo-2-thiazolidinyl]propyl}furan-2-carboxylic Acid This compound is prepared by a sequence of reactions analogous to those described in Example 13. An equivalent quantity of 5-methylfuran-2-carboxylic acid is substituted for the 5-methylthiophene-2-carboxylic acid employed in Example 13, Step A-1. The products thus obtained in this example are as follows:

Step A-1: Methyl 5-[4-tetrahydro-2H-pyran-2-yloxy)-butyl]furan-2-carboxylate;

Step A-2: Methyl 5-(4-hydroxybutyl)furan-2-carboxylate

Step A-3: Methyl 5-(4-oxobutyl)furan-2-carboxylate

Step C: Methyl 5-{3-[3-[2-(1-hydroxycyclohexyl)ethyl]-4-oxo-2-thiazolidinyl]propyl}furan-2-carboxylate Step D: 5-{3-[3-[2-(1-Hydroxycyclohexyl)ethyl]-4-oxo-2-thiazolidinyl]propyl}furan-2-carboxylic Acid

EXAMPLE 15

Preparation of 4-{3-[3-[2-(1-Hydroxycyclohexyl)ethyl]-5,5-dimethyl-4-oxo-2-thiazolidinyl]propyl}benzoic Acid Step A: Preparation of Ethyl 4-{3-[3-[2-(1-Hydroxycyclohexyl)ethyl]-5,5-dimethyl-4-oxo-2-thiazolidinyl]propyl}benzoate A solution of ethyl 4-(4-oxobutyl)benzoate (5.5 g., 0.025 mole) and 1-(2-aminoethyl)cyclohexanol (3.7 g., 0.026 mole) in toluene (40 ml.) is boiled in an open flask for 5 minutes to remove the formed water as the azeotrope. 2-Mercapto-2-methylpropionic acid (3.3 g., 0.0275 mole) is added and the solution is boiled under a Dean-Stark water separator for 5 hours. The solution is then cooled, washed with 2 N hydrochloric acid and water, and dried over sodium sulfate. The solvent is removed at reduced pressure. The residue is chromatographed on 165 g. of silica gel with 2% methanol in chloroform as the eluent. There is obtained 4.6 g. of the title ester as a light yellow, viscous oil.

Step B: Preparation of
4-{3-[3-[2-(1-Hydroxycyclohexyl)ethyl]-5,5-dimethyl-
4-oxo-2-thiazolidinyl]propyl}benzoic Acid The product of Step A above is saponified exactly as described in Example 2, Step C, to yield the title product as a crystalline solid, m.p. 132°–137° C. (from acetonitrile-water).

EXAMPLE 16

Preparation of
4-{3-[3-(3-Hydroxy-3-methyloctyl)-4-oxo-2-
thiazolidinyl]propyl}benzoic Acid This compound is prepared by the method described in Example 2, except that an equivalent quantity of 2-heptanone is substituted for the cyclohexanone employed in Example 2, Step A-1. There are thus obtained in the corresponding steps of this example:
Step A-1: 3-hydroxy-3-methylcaprylonitrile;
Step A-2: 3-(tetrahydro-2H-pyran-2-yloxy)-3-methylcaprylonitrile;
Step A-3: 1-amino-3-(tetrahydro-2H-pyran-2-yloxy)-3-methyloctane;

Step B: ethyl
4-{3-[3-(3-hydroxy-3-methyloctyl)-4-oxo-2-
thiazolidinyl]propyl}benzoate; and Step C:
4-{3-[3-(3-hydroxy-3-methyloctyl)-4-oxo-2-
thiazolidinyl]propyl}benzoic acid.

EXAMPLE 17

Preparation of
4-{3-[3-(3-Hydroxy-4,4-dimethyloctyl)-4-oxo-2-
thiazolidinyl]propyl}benzoic Acid This compound is prepared by the methods described in Example 1, Steps A through D, except that in Step B-1, an equivalent amount of 2,2-dimethylhexanal is substituted for the hexanal of Example 1, Step B-1. There are thus obtained successively in this example:
Step B-1: 3-hydroxy-4,4-dimethylcaprylonitrile;
Step B-2: 3-(tetrahydro-2H-pyran-2-yloxy)-4,4-dimethylcaprylonitrile;
Step B-3: 1-amino-3-(tetrahydro-2H-pyran-2-yloxy)-4,4-dimethyloctane;

Step C: ethyl
4-{3-[3-(3-hydroxy-4,4-dimethyloctyl)-4-oxo-2-
thiazolidinyl]propyl}benzoate; and Step D:
4-{3-[3-(3-hydroxy-4,4-dimethyloctyl)-4-oxo-2-
thiazolidinyl]propyl}benzoic acid.

EXAMPLE 18

Preparation of
4-{3-[3-(3-Hydroxydecyl)-4-oxo-2-thiazolidinyl]-
propyl}benzoic Acid This compound is prepared by the methods described in Example 1, Steps A through D, except that in Step B-1, an equivalent amount of octanal is substituted for the hexanal of Example 1, Step B-1. There are thus obtained successfully in this example:
Step B-1: 3-hydroxydecanonitrile;
Step B-2: 3-(tetrahydro-2H-pyran-2-yloxy)decanonitrile;
Step B-3: 1-amino-3-(tetrahydro-2H-pyran-2-yloxy)decane;

Step C: ethyl
4-{3-[3-(3-hydroxydecyl)-4-oxo-2-thiazolidinyl]-
propyl}benzoate; and Step D:
4-{3-[3-(3-hydroxydecyl)-4-oxo-2-thiazolidinyl]-
propyl}benzoic acid.

EXAMPLE 19

Preparation of
4-{3-[3-(3-Hydroxy-7-octenyl)-4-oxo-2-thiazolidinyl]-
propyl}benzoic Acid This compound is prepared by the methods described in Example 1, Steps A through D, except that in Step B-1, an equivalent amount of 5-hexenal is substituted for the hexanal of Example 1, Step B-1. There are thus obtained successively in this example:
Step B-1: 3-hydroxy-7-octenonitrile;
Step B-2: 3-(tetrahydro-2H-pyran-2-yloxy)-7-octenonitrile;
Step B-3: 1-amino-3-(tetrahydro-2H-pyran-2-yloxy)-7-octene;

Step C: ethyl
4-{3-[3-(3-hydroxy-7-octenyl)-4-oxo-2-thiazolidinyl]-
propyl}benzoate; and Step D:
4-{3-[3-(3-hydroxy-7-octenyl)-4-oxo-2-thiazolidinyl]-
propyl}benzoic acid.

EXAMPLE 20

Preparation of
4-{3-[3-(3-Hydroxy-8,8,8-trifluorooctyl)-4-oxo-2-
thiazolidinyl]propyl}benzoic Acid This compound is prepared by the methods described in Example 1, Steps A through D, except that in Step B-1, an equivalent amount of 6,6,6-trifluorohexanal is substituted for the hexanal of Example 1, Step B-1. There are thus obtained successively in this example:
Step B-1: 3-hydroxy-8,8,8-trifluorocaprylonitrile;
Step B-2: 3-(tetrahydro-2H-pyran-2-yloxy)-8,8,8-trifluorocaprylonitrile;
Step B-3: 1-amino-3-(tetrahydro-2H-pyran-2-yloxy)-8,8,8-trifluorooctane;

Step C: ethyl
4-{3-[3-(3-hydroxy-8,8,8-trifluorooctyl)-4-oxo-2-
thiazolidinyl]propyl}benzoate; and Step D:
4-{3-[3-(3-hydroxy-8,8,8-trifluorooctyl)-4-oxo-2-
thiazolidinyl]propyl}benzoic acid.

EXAMPLE 21

Preparation of
4-{3-[3-(3-Hydroxy-4-propoxybutyl)-4-oxo-2-
thiazolidinyl]propyl}benzoic Acid This compound is prepared by the methods described in Example 1, Steps A through D, except that in Step B-1, an equivalent quantity of propoxyacetaldehyde is substituted for the hexanal of Example 1, Step B-1. There are thus obtained successively in this example:
Step B-1: 3-hydroxy-4-propoxybutyronitrile;
Step B-2: 3-(tetrahydro-2H-pyran-2-yloxy)-4-propoxybutyronitrile;
Step B-3: 1-amino-3-(tetrahydro-2H-pyran-2-yloxy)-4-propoxybutane;

Step C: ethyl
4-{3-[3-(3-hydroxy-4-propoxybutyl)-4-oxo-2-thiazolidinyl]propyl}benzoate; and Step D:
4-{3-[3-(3-hydroxy-4-propoxybutyl)-4-oxo-2-thiazolidinyl]propyl}benzoic acid.

EXAMPLE 22

Preparation of
4-{3-[3-[2-(1-Hydroxycyclopentyl)ethyl]-4-oxo-2-thiazolidinyl]propyl}benzoic Acid This compound is prepared by the method described in Example 2, except that an equivalent quantity of cyclopentanone is substituted for the cyclohexanone employed in Example 2, Step A-1. There are thus obtained in the corresponding steps of this example:
Step A-1: 2-(1-hydroxycyclopentyl)acetonitrile;
Step A-2: 2-[1-(tetrahydro-2H-pyran-2-yloxy)cyclopentyl]acetonitrile;
Step A-3: 1-amino-2-[1-(tetrahydro-2H-pyran-2-yloxy)cyclopentyl]ethane;

Step B: ethyl
4-{3-[3-[2-(1-hydroxycyclopentyl)ethyl]-4-oxo-2-thiazolidinyl]propyl}benzoate; and Step C:
4-{3-[3-[2-(1-hydroxycyclopentyl)ethyl]-4-oxo-2-thiazolidinyl]propyl}benzoic acid.

The last named product of this invention is obtained as a crystalline solid, m.p. 149°-150° C. (from acetonitrile).

Anal. Calc'd for $C_{20}H_{27}NO_4S$: C, 63.63; H, 7.21; N, 3.71. Found: C, 63.62; H, 7.33; N, 3.66.

EXAMPLE 23

Preparation of
4-{3-[3-[2-(1-Hydroxycycloheptyl)ethyl]-4-oxo-2-thiazolidinyl]propyl}benzoic Acid This compound is prepared by the method described in Example 2, except that an equivalent quantity of cycloheptanone is substituted for the cyclohexanone employed in Example 2, Step A-1. There are thus obtained in the corresponding steps of this example:
Step A-1: 2-(1-hydroxycycloheptyl)acetonitrile;
Step A-2: 2-[1-(tetrahydro-2H-pyran-2-yloxy)cycloheptyl]acetonitrile;
Step A-3: 1-amino-2-[1-(tetrahydro-2H-pyran-2-yloxy)cycloheptyl]ethane;

Step B: ethyl
4-{3-[3-[2-(1-hydroxycycloheptyl)ethyl]-4-oxo-2-thiazolidinyl]propyl}benzoate; and Step C:
4-{3-[3-[2-(1-hydroxycycloheptyl)ethyl]-4-oxo-2-thiazolidinyl]propyl}benzoic acid.

The last named product of this invention is obtained as a crystalline solid, m.p. 146.5°-147.5° C. (from acetonitrile).

Anal. Calc'd for $C_{22}H_{31}NO_4S$: C, 65.15; H, 7.71; N, 3.45. Found: C, 64.80; H, 7.90; N, 3.36.

EXAMPLE 24

Preparation of
4-{3-[3-[2-(1-Hydroxy-4,4-dimethylcyclohexyl)ethyl]-4-oxo-2-thiazolidinyl]propyl}benzoic Acid This compound is prepared by the method described in Example 2, except that an equivalent quantity of 4,4-dimethylcyclohexanone is substituted for the cyclohexanone employed in Example 2, Step A-1. There are thus obtained in the corresponding steps of this example:
Step A-1: 2-(1-hydroxy-4,4-dimethylcyclohexyl)acetonitrile;
Step A-2: 2-[1-(tetrahydro-2H-pyran-2-yloxy)-4,4-dimethylcyclohexyl]acetonitrile;
Step A-3: 1-Amino-2-[1-(tetrahydro-2H-pyran-2-yloxy)-4,4-dimethylcyclohexyl]ethane;

Step B: Ethyl
4-{3-[3-[2-(1-hydroxy-4,4-dimethylcyclohexyl)ethyl]-4-oxo-2-thiazolidinyl]propyl}benzoate; and Step C:
4-{3-[3-[2-(1-hydroxy-4,4-dimethylcyclohexyl)ethyl]-4-oxo-2-thiazolidinyl]propyl}benzoic Acid.

The last named product of this invention is obtained as a crystalline solid, m.p. 142°-143° C. (from acetonitrile).

Anal. Calc'd for $C_{23}H_{33}NO_4S$: C, 65.84; H, 7.93; N, 3.34. Found: C, 65.71; H, 7.82; N, 3.62.

EXAMPLE 25

Preparation of
4-{3-[3-[2-(4-Hydroxytetrahydro-4-thiopyranyl)ethyl]-4-oxo-2-thiazolidinyl]propyl}benzoic Acid This compound is prepared by the method described in Example 2, except that an equivalent quantity of tetrahydrothiopyran-4-one is substituted for the cyclohexanone employed in Example 2, Step A-1. There are thus obtained in the corresponding steps of this example:
Step A-1: 2-(4-hydroxytetrahydro-4-thiopyranyl)acetonitrile;
Step A-2: 2-[4-(tetrahydro-2H-pyran-2-yloxy)-tetrahydro-4-thiopyranyl]acetonitrile;
Step A-3: 1-Amino-2-[4-(tetrahydro-2H-pyran-2-yloxy)tetrahydro-4-thiopyranyl]ethane;

Step B: Ethyl
4-{3-[3-[2-(4-hydroxytetrahydro-4-thiopyranyl)ethyl]-4-oxo-2-thiazolidinyl]propyl}benzoate; and Step C:
4-{3-[3-[2-(4-hydroxytetrahydro-4-thiopyranyl)ethyl]-4-oxo-2-thiazolidinyl]propyl}benzoic Acid.

The last named product of this invention is obtained as a crystalline solid, m.p. 157°-157.5° C. (from acetonitrile).

Anal. Calc'd for $C_{20}H_{27}NO_4S_2$: C, 58.65; H, 6.65; N, 3.42. Found: C, 58.41; H, 6.65; N, 3.33.

EXAMPLE 26

Preparation of
4-{3-[3-[2-(4-Hydroxytetrahydro-4-pyranyl)ethyl]-4-oxo-2-thiazolidinyl]propyl}benzoic Acid This compound is prepared by the method described in Example 2, except that an equivalent quantity of tetrahydropyran-4-one is substituted for the cyclohexanone employed in Example 2, Step A-1. There are thus obtained in the corresponding steps of this example:
Step A-1: 2-(4-hydroxytetrahydro-4-pyranyl)acetonitrile;
Step A-2: 2-[4-(tetrahydro-2H-pyran-2-yloxy)-tetrahydro-4-pyranyl]acetonitrile;
Step A-3: 1-Amino-2-[4-(tetrahydro-2H-pyran-2-yloxy)tetrahydro-4-pyranyl]ethane;

Step B: Ethyl 4-{3-[3-[2-(4-hydroxytetrahydro-4-pyranylethyl]-4-oxo-2-thiazolidinyl]propyl}benzoate; and Step C: 4-{3-[3-[2-(4-Hydroxytetrahydro-4-pyranyl)ethyl]-4-oxo-2-thiazolidinyl]propyl}benzoic acid.

EXAMPLE 27

Preparation of 4-{3-[3-[2-(9-Hydroxy-9-bicyclo[3.3.1]nonyl)ethyl]-4-oxo-2-thiazolidinyl]propyl}benzoic Acid This compound is prepared by the method described in Example 2, except that an equivalent quantity of bicyclo[3.3.1]nonan-9-one is substituted for the cyclohexanone employed in Example 2, Step A-1. There are thus obtained in the corresponding steps of this example:
Step A-1: 2-(9-hydroxy-9-bicyclo[3.3.1]nonyl)acetonitrile;
Step A-2: 2-[9-(tetrahydro-2H-pyran-2-yloxy)-9-bicyclo[3.3.1]nonyl]acetonitrile;
Step A-3: 1-amino-2-[9-(tetrahydro-2H-pyran-2-yloxy)-9-bicyclo[3.3.1]nonyl]ethane;

Step B: Ethyl 4-{3-[3-[2-(9-hydro-9-bicyclo[3.3.1]nonyl)ethyl]-4-oxo-2-thiazolidinyl]propyl}benzoate; and Step C: 4-{3-[3-[2-(9-hydroxy-9-bicyclo[3.3.1]nonyl)ethyl]-4-oxo-2-thiazolidinyl]propyl}benzoic Acid.

The last named product of this invention is obtained as a crystalline solid, m.p. 176.5°–178° C. (from acetonitrile).

Anal. Calc'd for $C_{24}H_{33}NO_4S$: C, 66.79; H, 7.71; N, 3.25. Found: C, 66.91; H, 7.46; N, 3.52.

EXAMPLE 28

Preparation of 4-{3-[3-(1-Hydroxycyclohexyl)-2-propynyl]-4-oxo-2-thiazolidinyl]propyl}benzoic Acid Step A: Preparation of Ethyl 4-{3-[3-(1-Acetoxycyclohexyl)-2-propynyl]-4-oxo-2-thiazolidinyl]propyl}benzoate This compound is prepared by the alkylation procedure described in Example 4, Step B, except that an equivalent quantity of 1-acetoxy-1-(3-bromo-1-propynyl)cyclohexane is substituted for the 1-(2-bromoethyl)cyclohexene used in Example 4, Step B. The title product is obtained as a yellowish viscous oil in 85% yield after chromatography on silica gel.

Step B: Preparation of 4-{3-[3-(1-Hydroxycyclohexyl)-2-propynyl]-4-oxo-2-thiazolidinyl]propyl}benzoic Acid The ester obtained in Step A above is saponified by the method described in Example 2, Step C. The crystalline product is purified by recrystallization from acetonitrile-butyl chloride, m.p. 112°–115° C. Anal. Calc'd for $C_{22}H_{27}NO_4S$: C, 65.81; H, 6.78; N, 3.49. Found: C, 65.07; H, 6.93; N, 3.29.

EXAMPLE 29

Preparation of 4-{3-[3-[3-(1-Hydroxycyclohexyl)-(Z)-2-propenyl]-4-oxo-2-thiazolidinyl]propyl}benzoic Acid 4-{3-[3-[3-(1-Hydroxycyclohexyl)-2-propynyl]-4-oxo-2-thiazolidinyl]propyl}benzoic acid (4.0 g., 0.01 mole) is dissolved in ethyl acetate (50 ml.) and hydrogenated at 25° C. and one atmosphere pressure over 1.0 g. of a 5% palladium on charcoal catalyst. The theoretical amount (0.01 mole) of hydrogen is absorbed in 110 minutes. The catalyst is removed by filtration and the solvent evaporated. The residual oil is chromatographed on 60 g. of silica gel with elution by 2% methanol is chloroform. The chromatographed product crystallizes and is recrystallized from butyl chloride to yield 1.4 g. of the title product, m.p. 118°–120° C.; pmr (CDCl₃) δ5.14 (1H, m, —CH₂—CH=), 5.60 (1H, d,

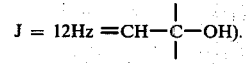

$J = 12Hz = CH-\overset{|}{\underset{|}{C}}-OH)$.

Anal. Calc'd for $C_{22}H_{29}NO_4S$: C, 65.48; H, 7.24; N, 3.47. Found: C, 65.47; H, 7.30; N, 3.32.

EXAMPLE 30

Preparation of 4-{3-[3-[3-(1-Hydroxycyclohexyl)propyl]-4-oxo-2-thiazolidinyl]propyl}benzoic Acid 4-{3-[3-[3-(1-Hydroxycyclohexyl)-2-propynyl]-4-oxo-2-thiazolidinyl]propyl}benzoic Acid (4.0 g., 0.01 mole) is dissolved in ethyl acetate (45 ml.) and hydrogenated at 25° C. and one atmosphere pressure over 1.0 g. of a 5% palladium on charcoal catalyst. When 0.01 mole of hydrogen is absorbed (2 hours), uptake of hydrogen becomes very slow. An additional 1.5 g. of catalyst is added and hydrogenation continued for 70 hours until 0.02 mole of hydrogen has been absorbed. The catalyst is removed by filtration and the solvent evaporated. The residual oil is chromatographed on silica gel with elution by 2% methanol in chloroform. The chromatographed product crystalizes when triturated with ether. There is obtained 1.2 g. of the title product, m.p. 118°–121° C.

Anal. Calc'd for $C_{22}H_{31}NO_4S$: C, 65.14; H, 7.71; N, 3.45. Found: C, 65.23; H, 7.66; N, 3.30.

EXAMPLE 31

Preparation of 4-{3-[3-[3-(1-Hydroxycyclohexyl)-(E)-2-propenyl]-4-oxo-2-thiazolidinyl]propyl}benzoic Acid Step A-1: Preparation of (E)-1-(3-Diethylamino-1-propenyl)cyclohexanol A stirred suspension of lithium tetrahydridoaluminate (1.13 g., 0.0299 mole) in ether (25 ml.) under N₂ is cooled in an ice bath to 0° C. and treated, dropwise, during 30 minutes, with a solution of 1-(3-diethylamino-1-propynyl)cyclohexanol (5.00 g., 0.0239 mole) in ether (5 ml.), while temperature is maintained 0°–5° C. After addition is complete, the cooling bath is removed and stirring is continued for 3 hours. The mixture is again cooled in an ice bath and the excess lithium tetrahydridoaluminate is decomposed by the cautious addition of saturated ammonium chloride solution (30 ml.). The mixture is filtered and the collected semi-solid is washed well with ether. The combined filtrate and washings are washed well with water and dried over anhydrous magnesium sulfate. The solvent is removed under vacuum to give the title compound as a yellow residual oil, yield 3.41 g.; pmr (CDCl$_3$) δ5.73 (2H, m. CH=CH).

Step A-2: Preparation of (E)-1-(3-Chloro-1-propenyl)-cyclohexanol (E)-1-(3-Diethylamino-1-propenyl)cyclohexanol (23.4 g., 0.11 mole) and potassium carbonate (1.0 g.) are added to ether (200 ml.). The mixture is stirred and treated dropwise during 30 minutes with a solution of ethyl chlorocarbonate (13.1 g., 0.12 mole) in ether (30 ml.). The reaction mixture is stirred for 18 hours at 25° C. It is then washed with 2 N hydrochloric acid and water, and dried over sodium sulfate. Vacuum distillation yields 11.7 g. of ethyl N,N-diethylcarbamate, b.p. 45°–50° C. (0.25 mm) and 7.4 g. of (E)-1-(3-chloro-1-propenyl)cyclohexanol, b.p. 88°–90° C. (0.25 mm.); pmr (CDCl$_3$) δ4.04 (2H, m, CH$_2$Cl), 5.80 (2H, m, CH=CH).

Step A-3: Preparation of (E)-1-(3-Chloro-1-propenyl)-1-(tetrahydro-2H-pyran-2-yloxy)cyclohexane A solution of (E)-1-(3-chloro-1-propenyl)cyclohexanol (6.1 g., 0.035 mole), dihydropyran (4.6 g., 0.055 mole) and pyridinium tosylate (0.5 g.) in dichloromethane (30 ml.) is kept at 25° C. for 3.5 hours. The solution is washed with saturated sodium bicarbonate solution and water and dried over sodium sulfate. Evaporation of the solvent at reduced pressure yields 9.0 g. of the title product as a yellowish oil which is used in the next step without further purification.

Step B: Preparation of Ethyl 4-{3-[3-[3-(1-(Tetrahydro-2H-pyran-2-yloxy)cyclohexyl)-(E)-2-propenyl]-4-oxo-2-thiazolidinyl]propyl}benzoate This compound is prepared by the alkylation procedure described in Example 4, Step B, except that an equivalent quantity of (E)-1-(3-chloro-1-propenyl)-1-(tetrahydro-2H-pyran-2-yloxy)cyclohexane is substituted for the 1-(2-bromoethyl)cyclohexene used in Example 4, Step B. The title product is obtained as a yellow, viscous oil after chromatography on silica gel.

Step C: Preparation of 4-{3-[3-[3-(1-Hydroxycyclohexyl)-(E)-2-propenyl]-4-oxo-2-thiazolidinyl]propyl}benzoic Acid A solution of the ester product of Step B above (4.5 g., 8.7 mmole) and pyridinium tosylate (220 mg., 0.87 mmole) in ethanol (50 ml.) is let stand at 25° C. for 2.5 hours. To this reaction solution is added a solution of sodium hydroxide (1.2 g., 30 mmole) in water (12 ml.). The resulting soluton is let stand at 25° C. for 20 hours. The ethanol is then evaporated at reduced pressure. The residue is dissolved in water, and the solution acidified with 2 N hydrochloric acid to precipitate the product as a yellow gum. It is chromatographed on 60 g. of silica gel with elution by 2% methanol in chloroform. The purified title product is obtained as a yellowish, viscous oil weighing 2.4 g.; pmr (CDCl$_3$) δ2.74 (2H, brt, CH$_2$Ph), 3.55 (2H, brs, COCH$_2$S), 4.70 (1H, brd, SCHN), 5.70 (2H, m, CH=CH), 6.53 (2H, brs, OH and CO$_2$H).

EXAMPLE 32

Preparation of Methyl 4-{3-[3-[2-(1-Hydroxycyclohexyl)ethyl]-4-oxo-2-thiazolidinyl]propyl}benzoate A solution of diazomethane (approximately 2.5 g., 0.06 mole) in ether (100 ml.) is mixed with a solution of 4-{3-[3-[2-(1-hydroxycyclohexyl)ethyl]-4-oxo-2-thiazolidinyl]propyl}benzoic acid (11.7 g., 0.03 mole) in ether (100 ml.). The resulting solution is allowed to stand at room temperature for 6 hours. Acetic acid is then added to destroy the excess diazomethane, and the solution is washed with dilute sodium bicarbonate solution and dried over sodium sulfate. Evaporation of volatile materials in vacuo yields the title compound as a nearly colorless, viscous oil.

EXAMPLE 33

Preparation of 4-{3-[3-[2-(1-Hydroxycyclohexyl)ethyl]-4-oxo-2-thiazolidinyl]propyl}benzoic Acid Hydrazide A solution of methyl 4-{3-[3-[2-(1-hydroxycyclohexyl)ethyl]-4-oxo-2-thiazolidinyl]propyl}benzoate (4.1 g., 0.01 mole) and hydrazine hydrate (2.5 g., 0.05 mole) in methanol (25 ml.) is stored at 25° C. for 48 hours. The solvent is then removed by distillation at reduced pressure. The residue is treated with water and enough 2 N hydrochloric acid to give a neutral mixture. The title compound is isolated by extraction into dichloromethane and subsequent drying and evaporation of the extract.

EXAMPLE 34

Preparation of N-Methylsulfonyl-4-{3-[3-[2-(1-hydroxycyclohexyl)ethyl]-4-oxo-2-thiazolidinyl]propyl}benzamide A solution of methanesulfonylisocyanate (1.33 g., 0.011 mole) in acetonitrile (10 ml.) is added dropwise during 10 minutes to a solution of 4-{3-[3-[2-(1-hydroxycyclohexyl)ethyl]-4-oxo-2-thiazolidinyl]propyl}benzoic acid (3.9 g., 0.01 mole) and triethylamine (1.0 g., 0.01 mole) in acetonitrile (30 ml.). The resulting solution is stored at 25° C. for 4 hours and then evaporated at reduced pressure. The residue is treated with water. The crude product is extracted into chloroform and purified by chromatography on a silica gel column with elution by 4% methanol in chloroform.

EXAMPLE 35

Preparation of 4-{3-[3-[2-(1-Acetoxycyclohexyl)ethyl]-4-oxo-2-thiazolidinyl]propyl}benzoic Acid A solution of 4-{3-[3-[2-(1-hydroxycyclohexyl)ethyl]-4-oxo-2-thiazoldinyl]propyl}benzoic acid (3.9 g., 0.01 mole) and acetic anhydride (1.2 g., 0.012 mole) in pyridine (15 ml.) is kept at 25° C. for 5 days. It is then poured into 50 ml. of ice water and the mixture brought to pH 5.0 by the addition of 2 N hydrochloric acid. The oily product is extracted into chloroform and purified by column chromatography on silica gel with elution by 2% methanol in chloroform.

EXAMPLE 36

Preparation of 4-{3-[3-[2-(1-Hydroxycyclohexyl)ethyl]-5,5-dideuterio-4-oxo-2-thiazolidinyl]propyl}benzoic Acid A solution of 4-{3-[3-[2-(1-hydroxycyclohexyl)ethyl]-4-oxo-2-thiazolidinyl]propyl}benzoic acid (391 mg., 1.0 mmole) and sodium hydroxide (160 mg., 4.0 mmoles) in deuterium oxide (5 ml.) is allowed to stand at 25° C. for 24 hours. The solution is acidified with 2 N hydrochloric acid to precipitate the crystalline product. This material is collected, washed with water, and air dried. There is obtained 288 mg. of the title compound, m.p. 146.5°–149° C.

The absence of the 2-proton signal at δ3.54 in the pmr spectrum shows that two deuterium atoms have been placed in the 5-position of the thiazolidinone ring.

What is claimed is:

1. A compound of the formula:

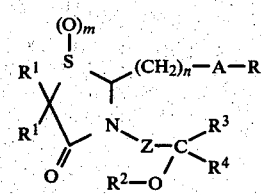

wherein

R is carboxy, a carboxy salt, a carboxy ester of the formula COOR$^5$ wherein R$^5$ is C$_{1-10}$ alkyl, or CONHR$^6$ wherein R$^6$ is amino or methylsulfonyl;

A is a p-phenylene or a m-phenylene or substituted phenylene derivative in which one or two of the phenylene hydrogens is replaced by a methyl or a halo substituent, or 2,5-thienylene or 2,5-furylene;

n is 3 or 4;

m is 0, 1, or 2;

R$^1$ is hydrogen, deuterium, or methyl;

Z is alkylene or unsaturated alkylene having from 2–3 carbon atoms;

R$^2$ is hydrogen or lower alkanoyl;

R$^3$ is hydrogen or straight chain C$_{1-3}$ alkyl; and

R$^4$ is lower straight chain or branched alkyl having from 3–7 carbon atoms, an unsaturated alkyl having from 3–7 carbon atoms, or a substituted lower alkyl selected from polyfluoro alkyl of from 3–7 carbon atoms and lower alkoxy methylene; or R$^3$ and R$^4$ taken together with the carbon atom connecting R$^3$ and R$^4$ is a cyclic substituent selected from a bridged or unbridged alicyclic ring of from 5–9 carbon atoms or a heterocyclic ring containing sulfur or oxygen and from 5–7 ring-forming carbon atoms.

2. The compound of claim 1 wherein R is carboxy or carboxy salt having the formula —COO$^-$M$^+$ wherein M$^+$ is a pharmaceutically acceptable cation derived from a metal or an amine.

3. The compound of claim 2 having the formula:

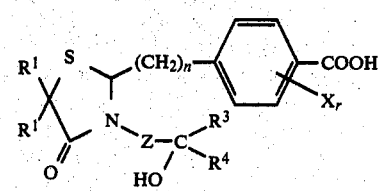

wherein

X is chlorine or methyl;

r is 0, 1, or 2;

n is 3 or 4;

R$^1$ is hydrogen, deuterium, or methyl;

Z is ethylene, trimethylene, cis or trans-propenylene, or propynylene;

R$^3$ is hydrogen or lower alkyl of 1–3 carbon atoms; and

R$^4$ is 4-pentenyl, 5,5,5-trifluoropentyl, or lower straight or branched chain alkyl of 3–7 carbon atoms.

4. The compound of claim 3 wherein r is 0, n is 3, and R$^1$ is hydrogen.

5. The compound of claim 4 wherein Z is ethylene.

6. 4-{3-[3-(3-Hydroxyoctyl)-4-oxo-2-thiazolidinyl]propyl}benzoic acid, the compound of claim 5 wherein R$^3$ is hydrogen and R$^4$ is pentyl.

7. 4-{3-[3-(3-Hydroxydecyl)-4-oxo-2-thiazolidinyl]propyl}benzoic acid, the compound of claim 5 where R$^3$ is hydrogen and R$^4$ is heptyl.

8. 4-{3-[3-(3-Hydroxy-4,4-dimethyloctyl)-4-oxo-2-thiazolidinyl]propyl}benzoic acid, the compound of claim 5 where R$^3$ is hydrogen and R$^4$ is 1,1-dimethylpentyl.

9. 4-{3-[3-(3-Hydroxy-7-octenyl)-4-oxo-2-thiazolidinyl]propyl}benzoic acid, the compound of claim 5 where R$^3$ is hydrogen and R$^4$ is 4-pentenyl.

10. 4-{3-[3-(3-Hydroxy-8,8,8-trifluorooctyl)-4-oxo-2-thiazolidinyl]propyl}benzoic acid, the compound of claim 5 where R$^3$ is hydrogen and R$^4$ is 5,5,5-trifluoropentyl.

11. 4-{3-[3-(3-Hydroxy-3-methyloctyl)-4-oxo-2-thiazolidinyl]propyl}benzoic acid, the compound of claim 5 where R$^3$ is methyl and R$^4$ is pentyl.

12. The compound of claim 2 having the formula:

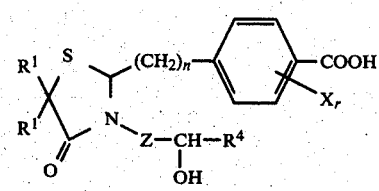

wherein

X is chlorine or methyl;

r is 0, 1, or 2;

n is 3 or 4;

R$^1$ is hydrogen, deuterium, or methyl;

Z is ethylene, trimethylene, cis or trans-propenylene, or propynylene; and

R$^4$ is CH$_2$OR$^7$ wherein R$^7$ is lower straight or branched chain alkyl of 2–5 carbon atoms.

13. The compound of claim 12 wherein r is 0, n is 3, and R$^1$ is hydrogen.

14. The compound of claim 13 wherein Z is ethylene.

15. 4-{3-[3-(3-Hydroxy-4-propoxybutyl)-4-oxo-2-thiazolidinyl]propyl}benzoic acid, the compound of claim 14 where R⁷ is propyl.

16. The compound of claim 2 having the formula:

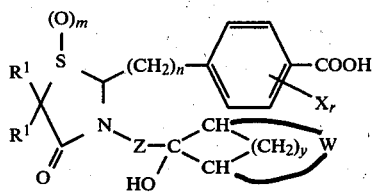

wherein
X is chlorine or methyl;
r is 0, 1, or 2;
n is 3 or 4;
m is 0, 1, or 2;
R¹ is hydrogen, deuterium, or methyl;
Z is ethylene, trimethylene, propenylene, or propynylene;
y is 0, 2, or 3; and
W is polymethylene of 2–6 carbon atoms.

17. The compound of claim 16 where r is 0, m is 0, and R¹ is hydrogen.

18. The compound of claim 17 where Z is ethylene.

19. 4-{3-[3-[2-(1-Hydroxycyclohexyl)ethyl]-4-oxo-2-thiazolidinyl]propyl}benzoic acid, the compound of claim 18 where n is 3, y is 0, and W is trimethylene.

20. 4-{3-[3-[2-(1-Hydroxycyclopentyl)ethyl]-4-oxo-2-triazolidinyl]propyl}benzoic acid, the compound of claim 18 where n is 3, y is 0, and W is ethylene.

21. 4-{3-[3-[2-(1-Hydroxycycloheptyl)ethyl]-4-oxo-2-thiazolidinyl]propyl}benzoic acid, the compound of claim 18 where n is 3, y is 0, and W is tetramethylene.

22. 4-{3-[3-[2-(1-Hydroxy-4,4-dimethylcyclohexyl)ethyl]-4-oxo-2-thiazolidinyl]propyl}benzoic acid, the compound of claim 18 where n is 3, y is 0, and W is 2,2-dimethyltrimethylene.

23. 4-{3-[3-[2-(9-Hydroxy-9-bicyclo[3.3.1]nonyl)ethyl]-4-oxo-2-thiazolidinyl]propyl}benzoic acid, the compound of claim 18 where n is 3, y is 3, and W is trimethylene.

24. 4-{4-[3-[2-(1-Hydroxycyclohexyl)ethyl]-4-oxo-2-thiazolidinyl]butyl}benzoic acid, the compound of claim 18 where n is 4, y is 0, and W is trimethylene.

25. The compound of claim 17 where Z is trimethylene.

26. 4-{3-[3-[3-(1-Hydroxycyclohexyl)propyl]-4-oxo-2-thiazolidinyl]propyl}benzoic acid, the compound of claim 25 where n is 3, y is 0, and W is trimethylene.

27. The compound of claim 17 where Z is cis-propenylene.

28. 4-{3-[3-[3-(1-Hydroxycyclohexyl)-(Z)-2-propenyl]-4-oxo-2-thiazolidinyl]propyl}benzoic acid, the compound of claim 27 where n is 3, y is 0, and W is trimethylene.

29. The compound of claim 17 where Z is trans-propenylene.

30. 4-{3-[3-[3-(1-Hydroxycyclohexyl)-(E)-2-propenyl]-4-oxo-2-thiazolidinyl]propyl}benzoic acid, the compound of claim 29 where n is 3, y is 0, and W is trimethylene.

31. The compound of claim 17 where Z is propynylene.

32. 4-{3-[3-[3-(1-Hydroxycyclohexyl)-2-propynyl]-4-oxo-2-thiazolidinyl]propyl}benzoic acid, the compound of claim 31 where n is 3, y is 0, and W is trimethylene.

33. The compound of claim 16 where X is chlorine, r is 1, m is 0, R¹ is hydrogen, and Z is ethylene.

34. 4-{3-[3-[2-(1-Hydroxycyclohexyl)ethyl]-4-oxo-2-thiazolidinyl]propyl}-3-chlorobenzoic acid, the compound of claim 33 where n is 3, y is 0, W is trimethylene, with chlorine in the 3-position of the phenylene group.

35. 4-{3-[3-[2-(1-Hydroxycyclohexyl)ethyl]-4-oxo-2-thiazolidinyl]propyl}-2-chlorobenzoic acid, the compound of claim 33 where n is 3, y is 0, W is trimethylene with chlorine in the 2-position of the phenylene group.

36. The compound of claim 16 where X is methyl, r is 1, m is 0, R¹ is hydrogen, and Z is ethylene.

37. 4-{3-[3-[2-(1-Hydroxycyclohexyl)ethyl]-4-oxo-2-thiazolidinyl]propyl}-3-methylbenzoic acid, the compound of claim 36 where n is 3, y is 0, W is trimethylene with methyl in the 3-position of the phenylene group.

38. The compound of claim 16 where m is 1, r is 0, R¹ is hydrogen, and Z is ethylene.

39. 4-{3-[3-[2-(1-Hydroxycyclohexyl)ethyl]-1,4-dioxo-2-thiazolidinyl]propyl}benzoic acid, the compound of claim 38 where n is 3, y is 0, and W is trimethylene.

40. The compound of claim 16 where m is 2, r is 0, R¹ is hydrogen, and Z is ethylene.

41. 4-{3-[3-[2-(1-Hydroxycyclohexyl)ethyl]-1,1,4-trioxo-2-thiazolidinyl]propyl}benzoic acid, the compound of claim 40 where n is 3, y is 0, and W is trimethylene.

42. The compound of claim 16 where m is 0, r is 0, R¹ is methyl, and Z is ethylene.

43. 4-{3-[3-[2-(1-Hydroxycyclohexyl)ethyl]-5,5-dimethyl-4-oxo-2-thiazolidinyl]propyl}benzoic acid, the compound of claim 42 where n is 3, y is 0, and W is trimethylene.

44. The compound of claim 16 where m is 0, r is 0, R¹ is deuterium, and Z is ethylene.

45. 4-{3-[3-[2-(1-Hydroxycyclohexyl)ethyl]-5,5-dideuterio-4-oxo-2-thiazolidinyl]propyl}benzoic acid, the compound of claim 44 where n is 3, y is 0, and W is trimethylene.

46. The compound of claim 2 having the formula:

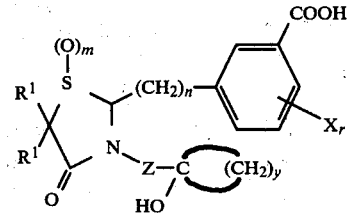

wherein
X is chlorine or methyl;
r is 0, 1, or 2;
n is 3 or 4;
m is 0, 1, or 2;
R¹ is hydrogen or methyl;
Z is ethylene, trimethylene, propenylene, or propynylene; and
y is 4 to 8.

47. The compound of claim 46 where r is 0, m is 0, R¹ is hydrogen, and Z is ethylene.

48. 3-{3-[3-[2-(1-Hydroxycyclohexyl)ethyl]-4-oxo-2-thiazolidinyl]propyl}benzoic acid, the compound of claim 47 where n is 3, and y is 5.

49. The compound of claim 2 having the formula:

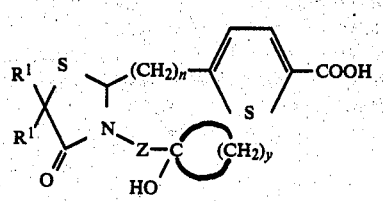

wherein
n is 3 or 4;
$R^1$ is hydrogen or methyl;
Z is ethylene, trimethylene, propenylene, or propynylene; and
y is 4 to 8.

50. 5-{3-[3-[2-(1-Hydroxycyclohexyl)ethyl]-4-oxo-2-thiazolidinyl]propyl}thiophene-2-carboxylic acid, the compound of claim 49 where n is 3, $R^1$ is hydrogen, Z is ethylene, and y is 5.

51. The compound of claim 2 having the formula:

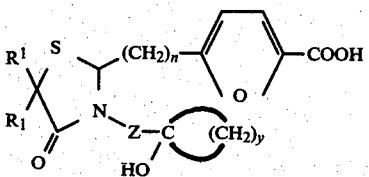

wherein
n is 3 or 4;
$R^1$ is hydrogen or methyl;
Z is ethylene, trimethylene, propenylene, or propynylene; and
y is 4 to 8.

52. 5-{3-[3-[2-(1-Hydroxycyclohexyl)ethyl]-4-oxo-2-thiazolidinyl]propyl}furan-2-carboxylic acid, the compound of claim 51 where n is 3, $R^1$ is hydrogen, Z is ethylene, and y is 5.

53. The compound of claim 2 having the formula:

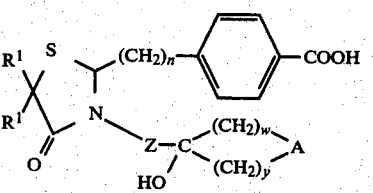

wherein
n is 3 or 4;
$R^1$ is hydrogen or methyl;
Z is ethylene, trimethylene, propenylene, or propynylene;
w and y are each 1 to 5 with the sum of w and y being from 4 to 6; and
A is oxygen or sulfur.

54. 4-{3-[3-[2-(4-Hydroxytetrahydro-4-pyranyl)ethyl]-4-oxo-2-thiazolidinyl]propyl}benzoic acid, the compound of claim 53 where n is 3, $R^1$ is hydrogen, Z is ethylene, w and y are each 2, and A is oxygen.

55. 44-{3-[3-[2-(4-Hydroxytetrahydro-4-thiopyranyl)ethyl]-4-oxo-2-thiazolidinyl]propyl}benzoic acid, the compound of claim 53 where n is 3, $R^1$ is hydrogen, Z is ethylene, w and y are each 2, and A is sulfur.

56. The compound of claim 1 wherein R is $COOR^5$ where $R^5$ is $C_{1-10}$ alkyl.

57. Methyl 4-{3-[3-[2-(1-hydroxycyclohexyl)ethyl]-4-oxo-2-thiazolidinyl]propyl}benzoate, the compound of claim 56 where A is unsubstituted p-phenylene (r=0), n is 3, m is 0, $R^1$ is hydrogen, $R^2$ is hydrogen, $R^3$ and $R^4$ are lower alkyl, joined to form a cyclohexane ring together with the carbon atom joining $R^3$ and $R^4$.

58. The compound of claim 1 wherein R is $CONHR^6$ where $R^6$ is amino and $R^2$ is hydrogen.

59. 4-{3-[3-[2-(1-Hydroxycyclohexyl)ethyl]-4-oxo-2-thiazolidinyl]propyl}benzoic acid hydrazide, the compound of claim 58 where A is unsubstituted p-phenylene (r=0), n is 3, m is 0, $R^1$ is hydrogen, and $R^3$ and $R^4$ are lower alkyl joined to form a cyclohexane ring together with the carbon atom joining $R^3$ and $R^4$.

60. The compound of claim 1 wherein R is $CONHR^6$ where $R^6$ is methylsulfonyl.

61. N-Methylsulfonyl-4-{3-[3-[2-(1-hydroxycyclohexyl)ethyl]-4-oxo-2-thiazolidinyl]propyl}benzamide, the compound of claim 60 where A is unsubstituted p-phenylene (r=0), n is 3, m is 0, $R^1$ and $R^2$ are hydrogen, and $R^3$ and $R^4$ are lower alkyl joined to form a cyclohexane ring together with the carbon atom joining $R^3$ and $R^4$.

62. The compound of claim 1 wherein R is carboxy, carboxy salt, or $COOR^5$ where $R^5$ is $C_{1-10}$ alkyl; and $R^2$ is acetyl.

63. 4-{3-[3-[2-(1-Acetoxycyclohexyl)ethyl]-4-oxo-2-thiazolidinyl]propyl}benzoic acid, the compound of claim 62 where R is carboxy, A is unsubstituted p-phenylene (r=0), n is 3, m is 0, $R^1$ is hydrogen, and $R^3$ and $R^4$ are lower alkyl joined to form a cyclohexane ring together with the carbon atom joining $R^3$ and $R^4$.

64. A pharmaceutical composition for improving renal function in patients with renal impairment comprising an aqueous, oily, or enteric-coated pharmaceutical carrier and an effective renal vasodilator amount of a compound of the formula:

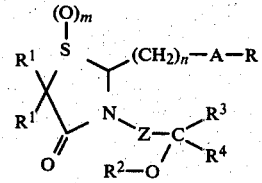

wherein
R is carboxy, a carboxy salt, a carboxy ester of the formula $COOR^5$ wherein $R^5$ is $C_{1-10}$ alkyl, or $CONHR^6$ wherein $R^6$ is amino or methylsulfonyl;
A is a p-phenylene or a m-phenylene or substituted phenylene derivative in which one or two of the phenylene hydrogens is replaced by a methyl or a halo substituent, or 2,5-thienyl or 2,5-furylene;
n is 3 or 4;
m is 0, 1, or 2;
$R^1$ is hydrogen, deuterium, or methyl;
Z is alkylene or unsaturated alkylene having from 2-3 carbon atoms;
$R^2$ is hydrogen or lower alkanoyl;
$R^3$ is hydrogen or straight chain $C_{1-3}$ alkyl; and
$R^4$ is a lower straight chain or branched alkyl having from 3-7 carbon atoms, an unsaturated alkyl having from 3-7 carbon atoms, or a substituted lower alkyl selected from polyfluoro alkyl of from 3–7 carbon atoms and lower alkoxy methylene; or $R^3$ and $R^4$ taken together with the carbon atom connecting $R^3$ and $R^4$ is a cyclic substituent selected from a bridged or unbridged alicyclic ring of from 5–9 carbon atoms or a heterocyclic ring containing sulfur or oxygen and from 5–7 ring-forming carbon atoms.

65. A composition of claim 64 wherein R is carboxy, A is phenyl, n is 3, m is 0, $R^1$ is hydrogen, Z is ethylene, $R^2$ is hydrogen, and $R^3$ and $R^4$ taken together with the carbon atom connecting $R^3$ and $R^4$ is cyclohexyl.

* * * * *